(12) United States Patent
Boudreaux et al.

(10) Patent No.: US 8,906,016 B2
(45) Date of Patent: Dec. 9, 2014

(54) SURGICAL INSTRUMENT FOR TRANSMITTING ENERGY TO TISSUE COMPRISING STEAM CONTROL PATHS

(75) Inventors: Chad P. Boudreaux, Cincinnati, OH (US); Terry A. McFarland, Burlington, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1023 days.

(21) Appl. No.: 12/576,831

(22) Filed: Oct. 9, 2009

(65) Prior Publication Data

US 2011/0087209 A1    Apr. 14, 2011

(51) Int. Cl.
*A61B 18/14* (2006.01)
*A61B 18/08* (2006.01)

(52) U.S. Cl.
CPC ......... *A61B 18/085* (2013.01); *A61B 2218/008* (2013.01)
USPC .............................................. 606/51; 606/52

(58) Field of Classification Search
USPC ............... 606/32, 37, 39, 40, 48, 50–52, 207; 607/99; 604/27, 45
See application file for complete search history.

(56) References Cited

U.S. PATENT DOCUMENTS

| | | | |
|---|---|---|---|
| 2,366,274 A | 1/1945 | Luth et al. |
| 2,458,152 A | 1/1949 | Eakins |
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,545,926 A | 10/1985 | Fouts, Jr. et al. |
| 4,582,236 A | 4/1986 | Hirose |
| 4,761,871 A | 8/1988 | O'Connor et al. |
| 4,849,133 A | 7/1989 | Yoshida et al. |
| 4,910,389 A | 3/1990 | Sherman et al. |

(Continued)

FOREIGN PATENT DOCUMENTS

DE      10201569 A1      7/2003
EP       0630612 A1     12/1994

(Continued)

OTHER PUBLICATIONS

International Search Report for PCT/US2010/051794, Jun. 8, 2011 (8 pages).

(Continued)

*Primary Examiner* — Michael Peffley
*Assistant Examiner* — Thomas Giuliani

(57) ABSTRACT

A surgical instrument for supplying energy to tissue can comprise an end effector comprising a first jaw member and a second jaw member, wherein at least one of the first jaw member and the second jaw member is movable relative to the other to clamp tissue intermediate the first jaw member and the second jaw member. The instrument can further include an electrode configured to generate heat when electrical energy is supplied to the electrode and, in addition, at least one steam path within the electrode, wherein the at least one steam path is configured to vent steam generated when the tissue is heated by the electrode.

13 Claims, 34 Drawing Sheets

(56) References Cited

U.S. PATENT DOCUMENTS

| | | |
|---|---|---|
| 5,104,025 A | 4/1992 | Main et al. |
| 5,106,538 A | 4/1992 | Barma et al. |
| 5,108,383 A | 4/1992 | White |
| 5,205,459 A | 4/1993 | Brinkerhoff et al. |
| 5,285,945 A | 2/1994 | Brinkerhoff et al. |
| 5,309,927 A | 5/1994 | Welch |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B2 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,267,685 B2 | 9/2007 | Butaric et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |

(56) References Cited

U.S. PATENT DOCUMENTS

| | | |
|---|---|---|
| 7,955,331 B2 | 6/2011 | Truckai et al. |
| 7,981,113 B2 | 7/2011 | Truckai et al. |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,298,232 B2 | 10/2012 | Unger |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2005/0273097 A1* | 12/2005 | Ryan ............................. 606/45 |
| 2006/0041254 A1* | 2/2006 | Francischelli et al. .......... 606/41 |
| 2006/0052778 A1 | 3/2006 | Chapman et al. |
| 2006/0064086 A1* | 3/2006 | Odom ............................. 606/51 |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0206140 A1 | 8/2009 | Scheib et al. |
| 2009/0209979 A1 | 8/2009 | Yates et al. |
| 2009/0248002 A1* | 10/2009 | Takashino et al. ............... 606/28 |
| 2009/0320268 A1 | 12/2009 | Cunningham et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2011/0087208 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0150176 A1 | 6/2012 | Weizman |

FOREIGN PATENT DOCUMENTS

| | | |
|---|---|---|
| EP | 0705571 A1 | 4/1996 |
| EP | 0640317 B1 | 9/1999 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/059741 A1 | 5/2009 |
| WO | WO 2009/082477 A2 | 7/2009 |

(56) References Cited

FOREIGN PATENT DOCUMENTS

| WO | WO 2010/017266 A1 | 2/2010 |
| WO | WO 2010/104755 A1 | 9/2010 |
| WO | WO 2011/089717 A1 | 7/2011 |

OTHER PUBLICATIONS

Kurt Gieck & Reiner Gieck, *Engineering Formulas* § Z.7 (7th ed. 1997).
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
Partial International Search Report for PCT/US2010/051794, Feb. 18, 2011 (2 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Humphrey, J.D., "Continuum Thermomechanics and the Clinical Treatment of Disease and Injury," Appl. Mech. Rev., vol. 56, No. 2 pp. 231-260 (Mar. 2003).
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
Wright, et al., "Time-Temperature Equivalence of Heat-Induced Changes in Cells and Proteins," Feb. 1998. ASME Journal of Biomechanical Engineering, vol. 120, pp. 22-26.
U.S. Appl. No. 13/221,410, filed Aug. 30, 2011.
U.S. Appl. No. 13/189,169, filed Jul. 22, 2011.

* cited by examiner

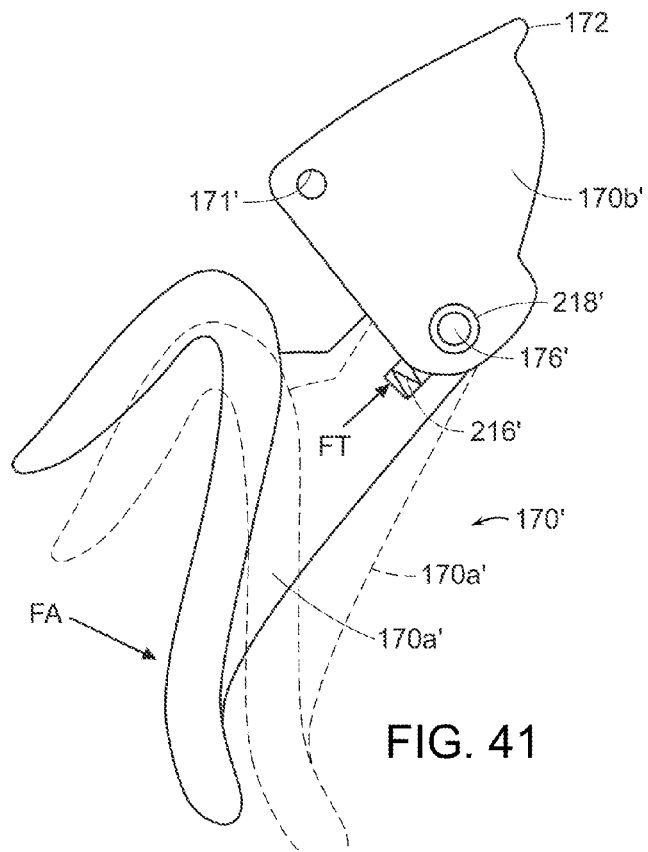
FIG. 41
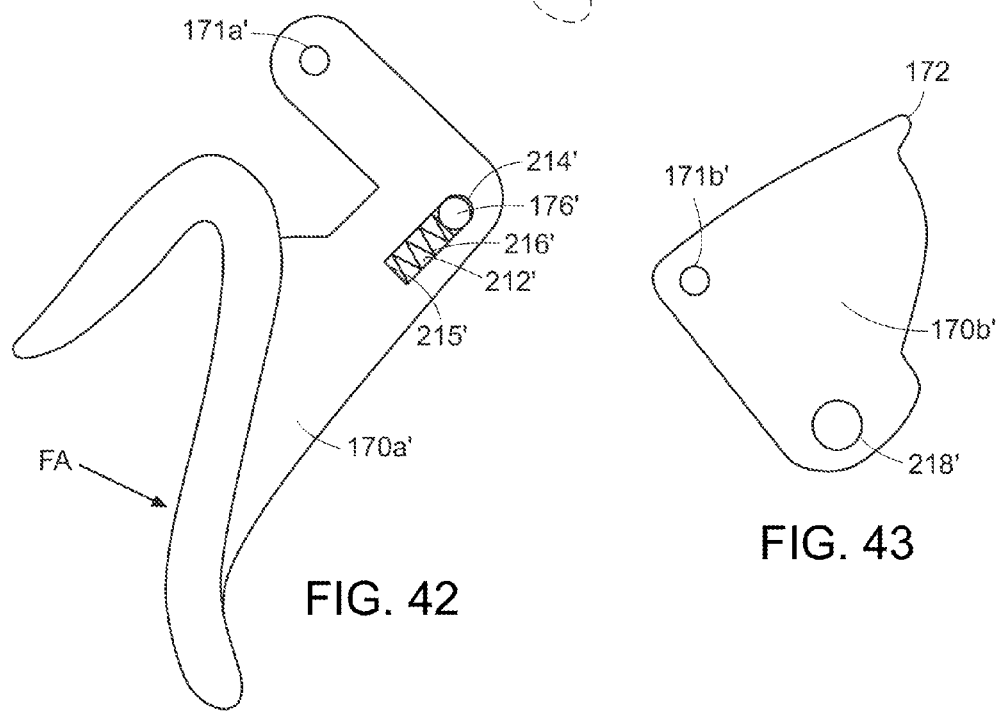
FIG. 42
FIG. 43

SURGICAL INSTRUMENT FOR TRANSMITTING ENERGY TO TISSUE COMPRISING STEAM CONTROL PATHS

BACKGROUND i. Field of the Invention

The present invention is directed to surgical instruments and methods for the use thereof.

ii. Description of the Related Art

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow through the electrodes and into the tissue. The surgical instrument can further comprise an electrical input, a supply conductor electrically coupled with the electrodes, and/or a return conductor which can be configured to allow current to flow from the electrical input, through the supply conductor, through the electrodes and tissue, and then through the return conductor to an electrical output, for example. In various circumstances, the current can generate heat within the electrodes wherein the heat can create one or more hemostatic seals within the tissue. Such embodiments may be particularly useful for sealing blood vessels, for example. The surgical instrument can further comprise a cutting member which can be moved relative to the tissue and electrodes in order to transect the tissue.

The foregoing discussion is intended only to illustrate various aspects of the related art in the field of the invention at the time, and should not be taken as a disavowal of claim scope.

SUMMARY

In at least one form, a surgical instrument can comprise an end effector comprising an electrode and a cutting member. The surgical instrument can further comprise an elongate shaft comprising a proximal end and a distal end, wherein said end effector is coupled to said distal end of said elongate shaft, and wherein said elongate shaft further comprises a conductor electrically coupled with said electrode. The surgical instrument can further comprise a drive shaft operably coupled with said cutting member. The surgical instrument can further comprise a handle coupled to said proximal end of said elongate shaft, wherein said handle comprises a lock movable between a locked position and an unlocked position, wherein said lock is engaged with said drive shaft to prevent said drive shaft from being advanced toward said distal end of said elongate shaft when said lock is in said locked position, and wherein said lock is disengaged from said drive shaft to permit said drive shaft to be advanced toward said distal end of said elongate shaft when said lock is in said unlocked position. The handle can further comprise an electrical input, and a switch movable between an unactuated position and an actuated position, wherein said electrical input is electrically uncoupled from said conductor when said switch is in said unactuated position, wherein said switch is configured to electrically couple said electrical input and said conductor when said switch is in said actuated position, and wherein said switch and said lock are operably coupled such that the movement of said switch from said unactuated position to said actuated position moves said lock from said locked position to said unlocked position.

In at least one form, a surgical instrument can comprise an end effector comprising an electrode and a cutting member, and an elongate shaft comprising a proximal end and a distal end, wherein said end effector is coupled to said distal end of said elongate shaft, and wherein said elongate shaft further comprises a conductor electrically coupled with said electrode. The surgical instrument can further comprise a drive shaft operably coupled with said cutting member. The surgical instrument can further comprise a handle coupled to said proximal end of said elongate shaft, wherein said handle comprises a lock movable between a locked position and an unlocked position, wherein said lock is engaged with said drive shaft to prevent said drive shaft from being advanced toward said distal end of said elongate shaft when said lock is in said locked position, and wherein said lock is disengaged from said drive shaft to permit said drive shaft to be advanced toward said distal end of said elongate shaft when said lock is in said unlocked position. The handle can further comprise an electrical input, and a switch movable between an unactuated position, an actuated position, and a third position, wherein said electrical input is electrically uncoupled from said conductor when said switch is in said unactuated position, wherein said switch is configured to electrically couple said electrical input and said conductor when said switch is in said actuated position, and wherein said switch and said lock are operably coupled such that the movement of said switch from said actuated position to said third position moves said lock from said locked position to said unlocked position.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise an end effector comprising a first jaw member and a second jaw member, wherein at least one of said first jaw member and said second jaw member is movable relative to the other of said first jaw member and said second jaw member to clamp tissue intermediate said first jaw member and said second jaw member. The end effector can further comprise an electrode electrically coupled with said conductor, wherein said electrode is configured to generate heat when electrical energy is supplied to said electrode, and at least one steam path within said electrode, wherein said at least one steam path is configured to vent steam generated when the tissue is heated by the electrode.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise an end effector comprising a first jaw member and a second jaw member, wherein at least one of said first jaw member and said second jaw member is movable relative to the other of said first jaw member and said second jaw member to clamp tissue intermediate said first jaw member and said second jaw member. The end effector can further comprise an electrode electrically coupled with said conductor, wherein said electrode is configured to generate heat when electrical energy is supplied to said electrode, a return electrode electrically coupled with said return conductor, and at least one steam path within said return electrode, wherein said at least one steam path is configured to vent steam generated when the tissue is heated by the electrode.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise an end effector comprising a first jaw member and a second jaw member, wherein at least one of said first jaw member and said second jaw member is movable relative to the other of said first jaw member and said second jaw member to clamp tissue intermediate said first jaw member and said second jaw member. The end effector can further comprise an electrode electrically coupled with said conductor, wherein said electrode is configured to generate heat when electrical energy is supplied to said electrode, and steam conduction means for conducting steam generated when the tissue is heated by the electrode.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise an end effector comprising a first jaw member and a second jaw member, wherein at least one of said first jaw member and said second jaw member is movable relative to the other of said first jaw member and said second jaw member to clamp tissue intermediate said first jaw member and said second jaw member. The end effector can further comprise an electrode electrically coupled with said conductor, wherein said electrode is configured to generate heat when electrical energy is supplied to said electrode, and a tissue-grasping portion comprising a plurality of teeth, wherein said tissue-grasping portion is comprised of an electrically non-conductive material.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise an end effector comprising a first jaw member and a second jaw member, wherein at least one of said first jaw member and said second jaw member is movable relative to the other of said first jaw member and said second jaw member to clamp tissue intermediate said first jaw member and said second jaw member. The end effector can further comprise an electrode electrically coupled with said conductor, wherein said electrode is configured to generate heat when electrical energy is supplied to said electrode, and an array of electrically non-conductive teeth positioned adjacent to and extending away from said electrode.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise a first jaw member comprising an electrode electrically coupled with said conductor, wherein said electrode is configured to generate heat when electrical energy is supplied to said electrode, and wherein said electrode comprises a top surface, and an insulator positioned adjacent to said electrode, wherein said insulator comprises a top surface movable between a first position and a second position relative to said top surface of said electrode, and wherein said top surface of said insulator is closer to said top surface of said electrode when said insulator is in said first position than when said insulator is in said second position. The surgical instrument can further comprise a second jaw member, wherein at least one of said first jaw member and said second jaw member is movable relative to the other of said first jaw member and said second jaw member to clamp tissue intermediate said first jaw member and said second jaw member.

In at least one form, a surgical instrument for supplying energy to tissue can comprise a handle comprising a trigger and an electrical input, and a shaft extending from said handle, wherein said shaft comprises a conductor, wherein said trigger is selectively actuatable to electrically couple said electrical input and said conductor. The surgical instrument can further comprise a first jaw member comprising an electrode electrically coupled with said conductor, wherein said electrode is configured to generate heat when electrical energy is supplied to said electrode, and wherein said electrode comprises a top surface, and an insulator positioned adjacent to said electrode, wherein said insulator is movable relative to said tissue-contacting surface between a first height and a second height, and wherein said insulator is positioned closer to said tissue-contacting surface when said insulator is at said first height than when said insulator is at said second height. The surgical instrument can further comprise a second jaw member, wherein at least one of said first jaw member and said second jaw member is movable relative to the other of said first jaw member and said second jaw member to clamp tissue intermediate said first jaw member and said second jaw member.

In at least one form, a surgical instrument for supplying energy to tissue can comprise a handle comprising a trigger and an electrical input, and a shaft extending from said handle, wherein said shaft comprises a conductor, and wherein said trigger is selectively actuatable to electrically couple said electrical input and said conductor. The surgical instrument can further comprise a first jaw member comprising an electrode electrically coupled with said conductor, wherein said electrode is configured to generate heat when electrical energy is supplied to said electrode, and wherein said electrode comprises a top surface, and an insulator positioned adjacent to said electrode, wherein said insulator comprises a top surface, wherein said top surface of said electrode is movable between a first position and a second position relative to said top surface of said insulator, and wherein said top surface of said electrode is closer to said top surface of said insulator when said electrode is in said first position than when said electrode is in said second position. The surgical instrument can further comprise a second jaw member, wherein at least one of said first jaw member and said second jaw member is movable relative to the other of said first jaw member and said second jaw member to clamp tissue intermediate said first jaw member and said second jaw member.

In at least one form, a surgical instrument can comprise a handle comprising a trigger movable between an unactuated position and an actuated position, a first drive system comprising a toggle clamp, and a second drive system. The second drive system can comprise a rack, a pinion operably engaged with said rack, and a yoke comprising a rack lock selectively engageable with said rack, wherein said trigger is movable between a first range of motion and a second range of motion when said trigger is moved between said unactuated position and said actuated position, wherein said trigger is operably engageable with said first drive system such that said trigger is configured to actuate said toggle clamp during said first range of motion, and wherein said trigger is operably engageable with said second drive system such that said trigger is configured to actuate said rack during said second range of motion. The surgical instrument can further comprise a shaft extending from said handle, wherein said shaft comprises a knife bar movable between a first position, a second position, and a third position, wherein said toggle clamp and said rack are operably engageable with said knife bar, wherein said toggle clamp is configured to move said knife bar between said first position and said second position, and wherein said rack is configured to move said knife bar between said second position and said third position. The surgical instrument can further comprise an end effector extending from said shaft, wherein said end effector comprises a distal end, a first jaw, and a second jaw, wherein said first jaw is movable relative to said second jaw between an open position and a closed position, wherein said knife bar is configured to move said first jaw between said open position and said closed position when said knife bar is moved between said first position and said second position, and wherein said knife bar is configured to move toward said distal end of said end effector when said knife bar is moved between said second position and said third position.

In at least one form, a surgical instrument configured to deliver energy to tissue can comprise a trigger movable between an unactuated position and an actuated position, a first drive system comprising a toggle clamp, and a second drive system comprising a rack and pinion system, wherein said trigger is movable between a first range of motion and a second range of motion when said trigger is moved between said unactuated position and said actuated position, wherein said trigger is operably engageable with said first drive system such that said trigger is configured to actuate said toggle clamp during said first range of motion, wherein said trigger is operably disengaged from said second drive system during said first range of motion, wherein said trigger is operably engageable with said second drive system such that said trigger is configured to actuate said rack during said second range of motion, and wherein said trigger is operable disengaged from said first drive system during said second range of motion. The surgical instrument can further comprise a shaft extending from said handle, wherein said shaft comprises a firing member movable between a first position, a second position, and a third position, wherein said toggle clamp and said rack are operably engageable with said firing member, wherein said toggle clamp is configured to move said firing member between said first position and said second position, and wherein said rack is configured to move said firing member between said second position and said third position. The surgical instrument can further comprise an end effector extending from said shaft, wherein said end effector comprises a distal end, a first jaw, and a second jaw, wherein said first jaw is movable relative to said second jaw between an open position and a closed position, and wherein said firing member is configured to move said first jaw between said open position and said closed position when said firing member is moved between said first position and said second position, and wherein said firing member is configured to move toward said distal end of said end effector when said firing member is moved between said second position and said third position.

The foregoing discussion should not be taken as a disavowal of claim scope.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 9 further illustrates a portion of the first drive system of FIG. 4 in an unactuated configuration.

FIG. 21 also illustrates the trigger of FIG. 4 and the rack of FIG. 18 in a partially retracted, or partially returned, position.

FIG. 23 also illustrates the rack of FIG. 18 in a further partially retracted, or further partially returned, position and the lock system of FIG. 9 re-engaged with the rack of FIG. 18.

FIG. 32 further illustrates a button switch of the lock system in an unactuated configuration.

FIG. 41 illustrates a trigger assembly of an alternative embodiment of a surgical instrument, wherein the trigger assembly further comprises a mechanism for limiting the force that can be transmitted through the trigger assembly. FIG. 41 further illustrates a first part of the trigger assembly (illustrated with phantom lines) moved relative to a second part of the trigger assembly.

FIG. 42 is an elevational view of the first part of the trigger assembly.

FIG. 43 is an elevational view of the second part of the trigger assembly.

FIG. 44 further illustrates a first part of the trigger assembly (illustrated with phantom lines) moved relative to a second part of the trigger assembly.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
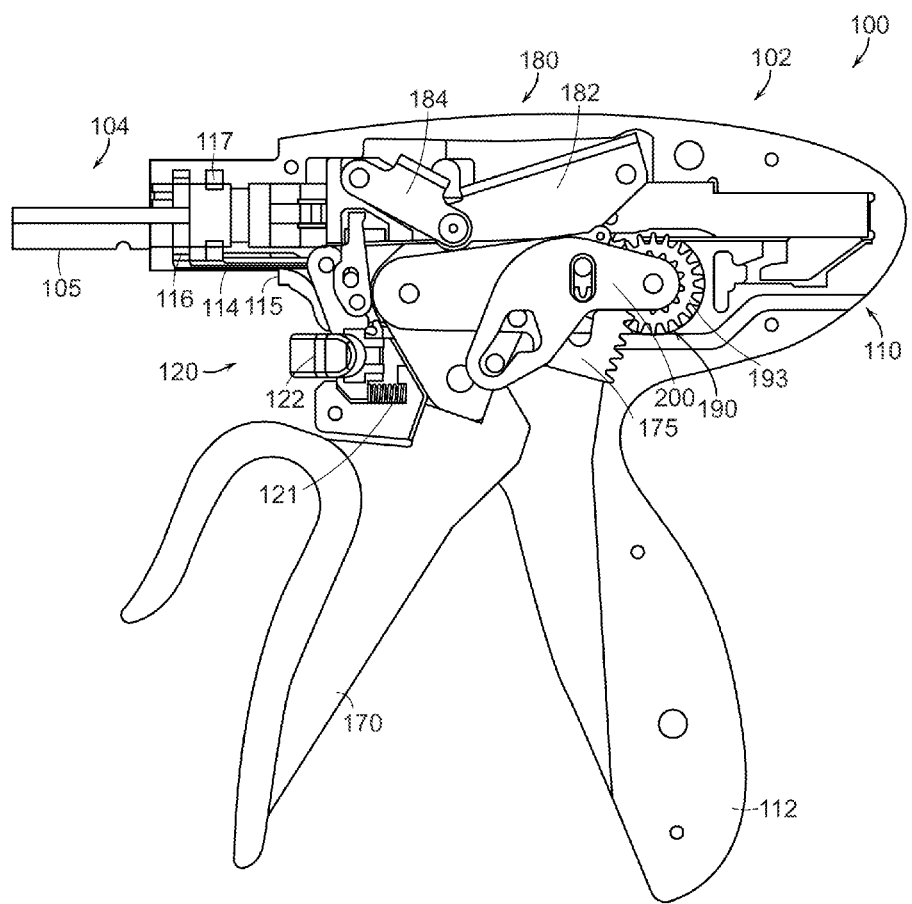
FIG. 1 is a cross-sectional view of a handle of a surgical instrument illustrated with some components removed in accordance with at least one embodiment.

Various embodiments are directed to apparatuses, systems, and methods for the treatment of tissue Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The entire disclosures of the following commonly-owned, non-provisional United States patent applications are hereby incorporated by reference herein:

U.S. patent application Ser. No. 12/576,756, now U.S. Patent Publication No. 2011/0087220, entitled SURGICAL INSTRUMENT COMPRISING AN ENERGY TRIGGER LOCKOUT, filed on even date herewith;

U.S. patent application Ser. No. 12/576,789, now U.S. Patent Publication No. 2011/0087219, entitled SURGICAL INSTRUMENT FOR TRANSMITTING ENERGY TO TISSUE COMPRISING NON-CONDUCTIVE GRASPING PORTIONS, filed on even date herewith;

U.S. patent application Ser. No. 12/576,808, now U.S. Patent Publication No. 2011/0087208, entitled SURGICAL INSTRUMENT FOR TRANSMITTING ENERGY TO TISSUE COMPRISING A MOVABLE ELECTRODE OR INSULATOR, filed on even date herewith; and U.S. patent application Ser. No. 12/576,776, now U.S. Patent Publication No. 2011/0087218, entitled SURGICAL INSTRUMENT COMPRISING FIRST AND SECOND DRIVE SYSTEMS ACTUATABLE BY A COMMON TRIGGER MECHANISM, filed on even date herewith.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Figure 3:
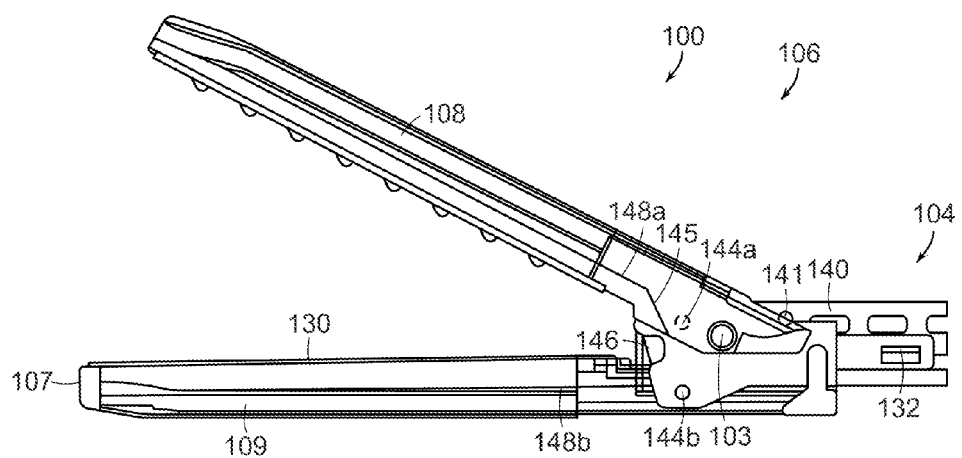
FIG. 3 is an elevational view of an end effector of the surgical instrument of FIG. 1 illustrated in an open configuration and the distal end of a knife bar in an unadvanced position.

A surgical instrument can be configured to supply energy, such as electrical energy and/or heat energy, for example, to the tissue of a patient. In various embodiments, referring now to FIG. 1, a surgical instrument, such as surgical instrument 100, for example, can comprise a handle 102, a shaft 104, and an end effector 106 (FIG. 3). As described in greater detail below, the handle 102 can comprise one or more switches or triggers which can be configured to supply electrical energy to end effector 106 and/or advance a knife or cutting member within the end effector 106, for example, in order to transect the tissue positioned within the end effector 106.

In various embodiments, referring to FIG. 1, the handle 102 can comprise one or more electrical inputs, such as input, or terminal, 110, for example, which can be operably coupled with a power supply, such as a voltage supply, for example. In various embodiments, such a power supply can provide an electrical current to the surgical instrument 100, wherein the magnitude, duration, wave form, and/or frequency, for example, of the current can be sufficiently controlled or modulated to provide a desired amount of energy to the surgical instrument 100. Such power supplies are well known within the art and a more detailed description thereof is not required. In various embodiments, the handle 102 can comprise a handle body 112 which, as described in greater detail below, can be configured to operably support a switch or trigger, such as trigger system 120, for example, which can be configured to electrically couple electrical input 110 with a conductor in shaft 104 such that the current supplied to input 110 can be transmitted to end effector 106. In various embodiments, referring to FIG. 1, handle body 112 can comprise two portions which are assembled together to form handle body 112. As the reader will note, only one of the portions, or halves, is depicted in FIG. 1, although the other portion, or half, can be a mirror image of, or at least substantially similar to, the half depicted in FIG. 1. In various embodiments, the halves of handle body 112 can be snap-fit, press-fit, adhered, and/or fastened to one another.

In various embodiments, further to the above, the electrical conductor within the shaft 104 can comprise a wire, such as insulated wire, for example, which can extend between trigger system 120 and an electrode 130 (FIG. 3) in end effector 106. In certain embodiments, referring again to FIG. 1, the handle 102 can further comprise a supply wire 114 which can be electrically coupled with an electrical supply conductor (not illustrated) encased within an outer housing, or spine, 105 (FIG. 8) of the shaft 104. In at least one embodiment, the supply conductor can comprise a conductive insert, comprised of copper, for example, which is at least partially positioned within an insulative plastic jacket or sheath, for example, of the spine 105. In certain circumstances, the plastic jacket can be molded over the conductive insert during an injection molding process. In various embodiments, referring again to FIG. 1, the handle 102 can comprise a slip ring 116 which can be configured to electrically couple wire 114 with the supply conductor within shaft 104. More particularly, in at least one embodiment, the slip ring 116 can comprise a circular, or an at least semi-circular, contact, for example, mounted to handle body 102 which can remain in contact with a corresponding circular, or an at least semi-circular, contact mounted to shaft 104. Such corresponding contacts can permit relative rotational movement between shaft 104 and handle 102 and yet still provide an electrical path between wire 114 and the electrical supply conductor within shaft 104.

In various embodiments, the shaft 104 can further comprise another slip ring connector which, similar to the above, can maintain electrical contact between the supply conductor of shaft 104 and a supply contact 132 (FIG. 3) of electrode 130. As described in greater detail below, electrical current can flow from the electrical input 110, through supply wire 114, through the electrical conductor in shaft 104, and into the electrode 130 such that current can flow from the electrode 130 and into the tissue captured within the end effector 106. In various embodiments, as also described in greater detail below, the end effector can further comprise one or more return electrodes and/or conductors which can comprise a return path, or circuit, for the current. In at least one embodiment, similar to the above, the return path can comprise a slip ring contact operably coupled with a return electrode in the end effector 106 and a return conductor embedded within the shaft 104, for example. Also similar to the above, the handle 102 can further comprise a slip ring 117, for example, which can maintain the return conductor within shaft 104 in electrical contact with return wire 115. In at least one such embodiment, the return wire 115 can extend between the slip ring 117 and an electrical output, or terminal, which can, in various embodiments, be positioned adjacent to electrical input, or terminal, 110.

Figure 37:
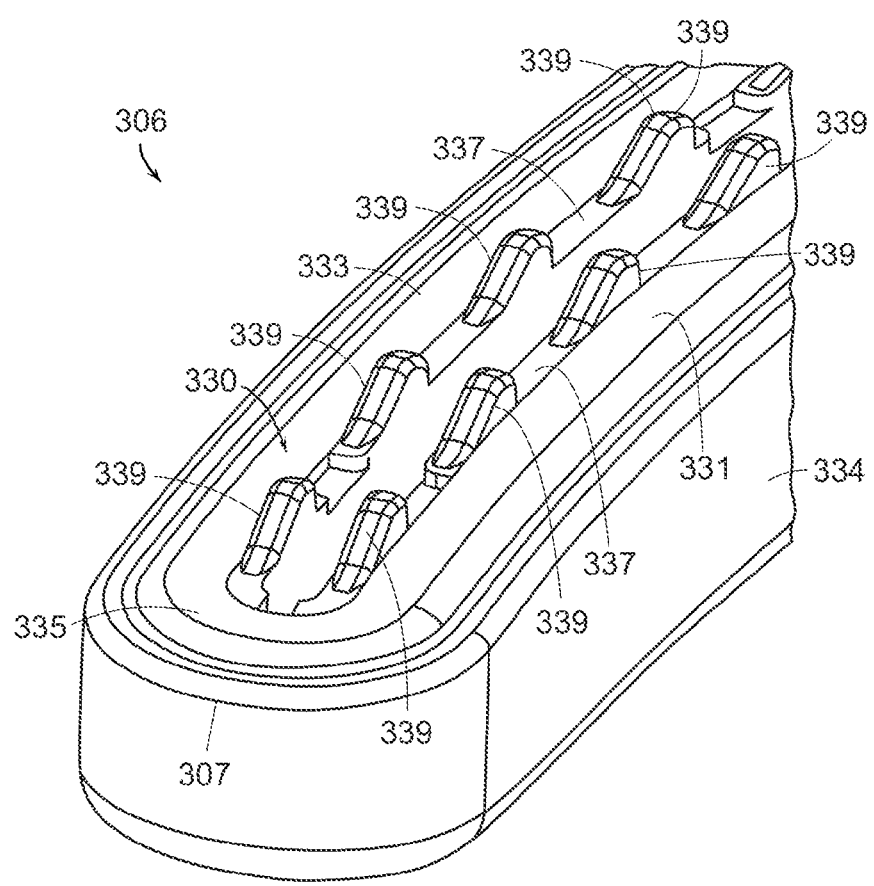
FIG. 37 illustrates a jaw of an end effector in accordance with at least one embodiment.

Further to the above, referring to FIG. 37, an end effector 306 can comprise an electrode 330 which can extend between a proximal end of end effector 306 and a distal end 307 of end effector 306. In at least one such embodiment, the electrode 330 can comprise a first lateral portion 331 extending along a first side of jaw member 334, a second lateral portion 333 extending along a second side of jaw member 334, and a transverse intermediate portion 335 connecting the first lateral portion 331 and the second lateral portion 333. In various embodiments, further to the above, the first jaw member can further comprise a return electrode and/or the end effector can further comprise a second jaw member having a return electrode which can be positioned opposite the first jaw member. In any event, referring again to FIG. 1, the trigger system 120 can comprise a button 122 which can be selectively actuated in order to electrically couple the electrical input 110 with supply wire 114 and/or selectively actuated in order to electrically couple the return wire 115 with the electrical output of handle 102. More particularly, in at least one embodiment, the button 122 can be movable between an undepressed, or unactuated, position in which current cannot flow to electrode 130, and a depressed, or actuated, position in which current can flow to electrode 130. Although the button 122, and/or any similar button, can be used to actuate the switch 123, and/or any other suitable switch, other energy actuation mechanisms, such as toggles, levers, and/or any suitable actuators, can be used in addition to or in lieu of the above.

When electrical current is supplied to an electrode, referring again to FIG. 37, the electrical current can pass through the tissue positioned against and/or surrounding the electrode 330, for example. In various circumstances, the current flowing through the electrode 330 can generate heat within the electrode and the surrounding tissue. In certain circumstances, the heat can denature the collagen within the tissue and, in co-operation with clamping pressure provided by the jaws of the end effector, the denatured collagen can form a seal within the tissue, for example. In at least one circumstance, the first side 331 of electrode 330 can be configured to create a first seal within the tissue and the second side 333 of electrode 330 can be configured to create a second seal within the tissue. Other embodiments are envisioned in which multiple electrodes, and/or multiple electrode portions, can create any suitable number of seals within the tissue. In various embodiments, as described in greater detail below, one or more of the jaw members of an end effector can comprise grasping portions which can be utilized to manipulate tissue within a surgical site and/or position and hold the tissue within the end effector.

In at least one embodiment, referring to FIG. 37, first jaw member 334 can comprise at least one grasping member, such as a grasping portion 337, for example, which can be comprised of an electrically non-conductive, or insulative, material, such as plastic and/or ceramic, for example. In use, the grasping portions 337 can hold the tissue within the end effector without conducting, or at least not significantly conducting, current and/or heat to the tissue. In various embodiments, as a result, the possibility of the treated tissue adhering to, or becoming stuck to, the grasping portions 337 can be reduced or eliminated. In various embodiments, each grasping portion 337 can comprise an array or row of teeth 339, for example, wherein, in at least one embodiment, a first grasping portion can comprise a first array or row of teeth 339 and a second grasping portion can comprise a second array or row of teeth 339. In at least one such embodiment, the first row of teeth 339 can be positioned adjacent to the first lateral portion 331 of electrode 330 and the second row of teeth 339 can be positioned adjacent to the second lateral portion 333 of electrode 330.

In various circumstances, further to the above, the grasping portions 337 can be comprised of an electrically non-conductive plastic, glass, and/or ceramic, for example, and, in at least one embodiment, the grasping portions 337 can be formed by an injection molding process. In certain embodiments, at least one lubricant additive, such as a TEFLON coating, for example, can be mixed or embedded within the plastic. In various circumstances, the one or more lubricants can prevent, or at least inhibit, the tissue captured within the end effector 306 from sticking or adhering to the teeth 339, for example. In addition to or in lieu of the above, in certain embodiments, at least one lubricant, such as a TEFLON coating, for example, can be coated on the grasping portions 337. In certain embodiments, the grasping portions 337 can be comprised of an electrically conductive material which can be coated, or at least partially coated, with an electrically non-conductive material, for example.

Owing to current flowing through the tissue and/or the heat generated by the one or more electrodes of an end effector of the surgical instrument, water, and/or other fluids, within the tissue can be vaporized. In certain circumstances, the heated vapors, such as steam, for example, can flow out of the end effector and into the surgical site surrounding the end effector.

Figure 38:
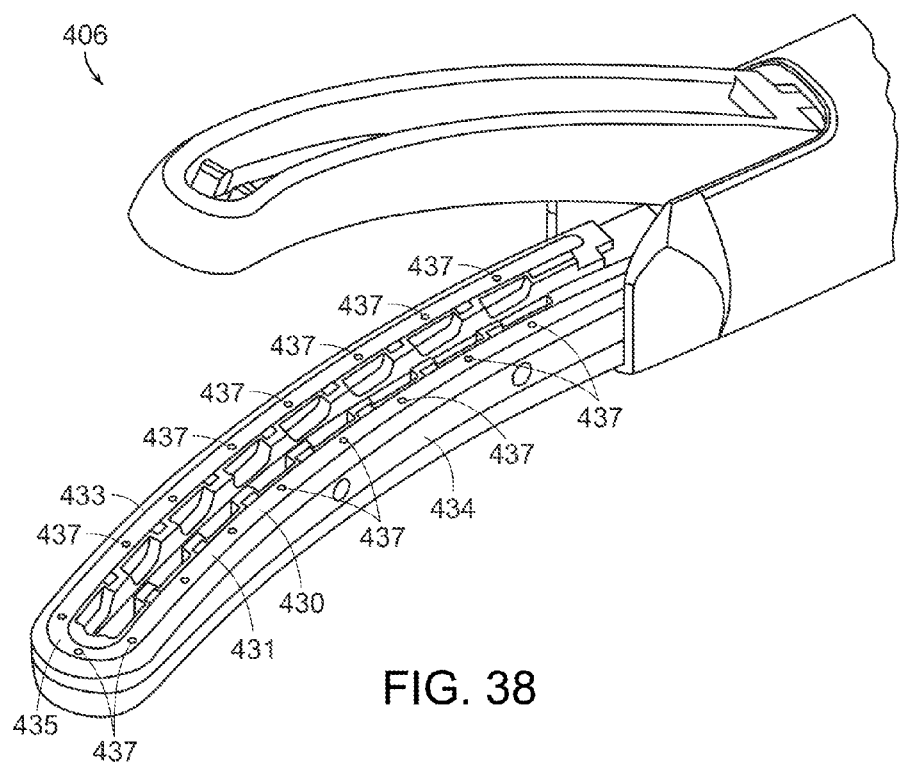
FIG. 38 illustrates a jaw of an end effector comprising steam control paths in accordance with at least one embodiment.
Figure 38A:
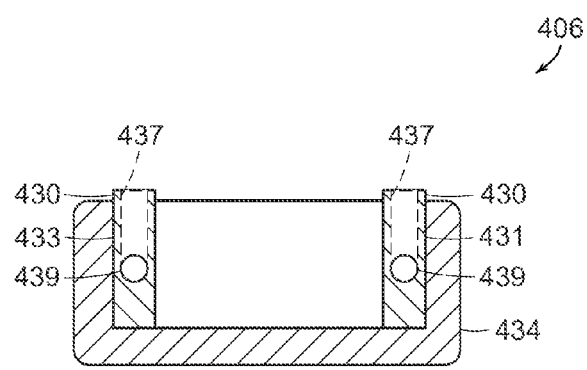
FIG. 38A is a cross-sectional view of the jaw of FIG. 38 illustrating the steam control paths extending through an electrode of the end effector. Various components of the end effector have been removed in FIG. 38A.

In various circumstances, the heated vapors can damage the surrounding tissue. In various embodiments, referring now to FIG. 38, at least one of the jaws, such as first jaw 434, for example, of end effector 406 can comprise at least one steam control path, passage, or conduit for conveying the steam, and/or other vapors created by the current and/or heat, away from the surgical site. In certain embodiments, an electrode, such as electrode 430, for example, can comprise an electrode body and at least one steam control path therein. In at least one embodiment, referring to FIG. 38A, the steam control path can comprise one or more passages 439 which can extend longitudinally through the first lateral portion 431 and the second lateral portion 433 of electrode 430, for example. The steam control paths can further comprise one or more passages, or holes, 437 which can extend between an outside surface of electrode 430 and the passages 439 such that steam can flow from the tissue being treated, through the holes 437, and into the passages 439. In at least one embodiment, the passage 439 extending though the first lateral portion 431 and the passage 439 extending through the second lateral portion 433 can be in fluid communication via a passage within intermediate portion 435 of electrode 430. In various embodiments, the shaft of the surgical instrument, such as shaft 104 of surgical instrument 100, for example, can comprise one or more passages or conduits therein which can be in fluid communication with the passages 439, for example, such that the heated vapors can be conveyed away from the end effector and out of the patient. In at least one such embodiment, the handle of the surgical instrument, such as handle 102, for example, can comprise at least one vent configured to allow the heated vapors to vent into the atmosphere surrounding the patient, for example.

Figure 38B:
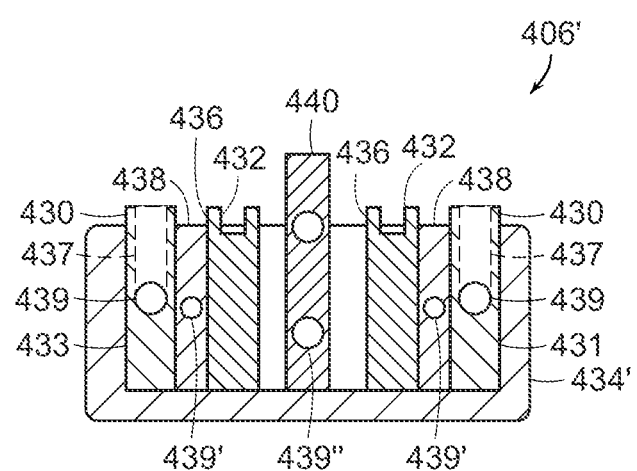
FIG. 38B is a cross-sectional view of a jaw of an alternative embodiment of an end effector illustrating steam control paths in supply electrodes, return electrodes, insulators positioned intermediate the supply electrodes and the return electrodes, and a cutting member movable within the end effector.

In various embodiments, referring now to FIG. 38B, a jaw 434' of an end effector 406' can comprise, similar to the above, a supply electrode 430 having first and second portions 431, 433 and steam control paths comprising passages 437, 439 extending therethrough. The end effector 406' can further comprise at least one return electrode 436 and one or more electrically non-conductive insulators 438 positioned intermediate portions of the supply electrode 430 and portions of the return electrode 436. In various embodiments, the return electrode and/or the insulators can comprise one or more steam control paths for conveying steam away from the tissue being treated. For example, the return electrode can comprise one or more channels 432 therein which can be configured to convey the steam in a space intermediate the tissue and an outside surface of the return electrode 436. Also, for example, the insulators 438 can comprise one or more passages 439' extending therethrough. Although passages 437, 439, and 439' are illustrated as comprising round, or at least substantially round, elongate configurations, the passages extending through the supply electrode, the return electrode, and/or the insulators can comprise any suitable configuration, such as square and/or rectangular configurations, for example. Furthermore, although channels 432 are illustrated as having substantially orthogonal sidewalls, the sidewalls of the channels can comprise any suitable configuration, such as arcuate and/or semi-circular configurations, for example. In any event, any one of the supply electrode, return electrode, and/or insulators can comprise any suitable number of exterior channels and/or internal passages therein for conveying heated vapors away from the tissue in the end effector. In certain embodiments, referring again to FIG. 38B, a cutting member 440 can comprise one or more steam paths 439" extending therethrough.

As described above, electrical energy, or current, can be supplied to the electrodes of an end effector, such as electrode 130 of end effector 106, for example, in order to treat, heat, and/or seal tissue captured within the end effector 106. As also described above, the tissue can be transected by a knife or cutting member. In various circumstances, however, it may not be desirable to transect the tissue prior to supplying electrode 130 with current and/or prior to the application of heat to the tissue. In various embodiments described herein, surgical instrument 100, for example, can comprise a trigger system, such as trigger system 120, for example, which can be configured to prevent the cutting member 140 (FIG. 3) of surgical instrument 100 from being advanced toward the distal end 107 of end effector 106 prior to the electrical current being supplied to electrode 130. In certain embodiments, the cutting member 140 can be advanced at the same time that current is supplied to electrode 130. In certain other embodiments, the current can be supplied to electrode 130 prior to cutting member 140 being advanced to transect the tissue.

In various embodiments, referring now to FIGS. 31-36, the trigger system 120 can comprise an energy actuation button 122 mounted to a first link 124, a second link 126 operably coupled with first link 124, and a pivotable lock 150 which can be moved between a locked position and an unlocked position by second link 126. The button 122 can be moveable between an unactuated, or undepressed, position (FIG. 32) and an actuated, or depressed, position (FIG. 33) in order to electrically connect, or couple, a first portion 114a of supply wire 114 and a second portion 114b of supply wire 114. More particularly, the trigger system 120 can further comprise a switch 123 mounted to first link 124 which can be switched, or closed, when button 122 is depressed such that current can flow from the electrical input 110, through the first supply wire portion 114a, and into the second supply wire portion 114b and slip ring 116. As described above, the current can then flow to electrode 130, through return wire 117, and then through the electrical outlet in order to complete the electrical circuit. In various embodiments, the switch 123 can comprise a spring, such as a linear coil spring, for example, positioned therein which can be compressed when the button 122 is moved from its unactuated position to its actuated position. In at least one such embodiment, the coil spring can be positioned intermediate the button 122 and a housing of the switch 123 and/or first link 124. In any event, in certain embodiments, a force is required to compress the spring and, in addition, the button 122 is required to move a predetermined distance in order to actuate switch 123.

Figure 32:
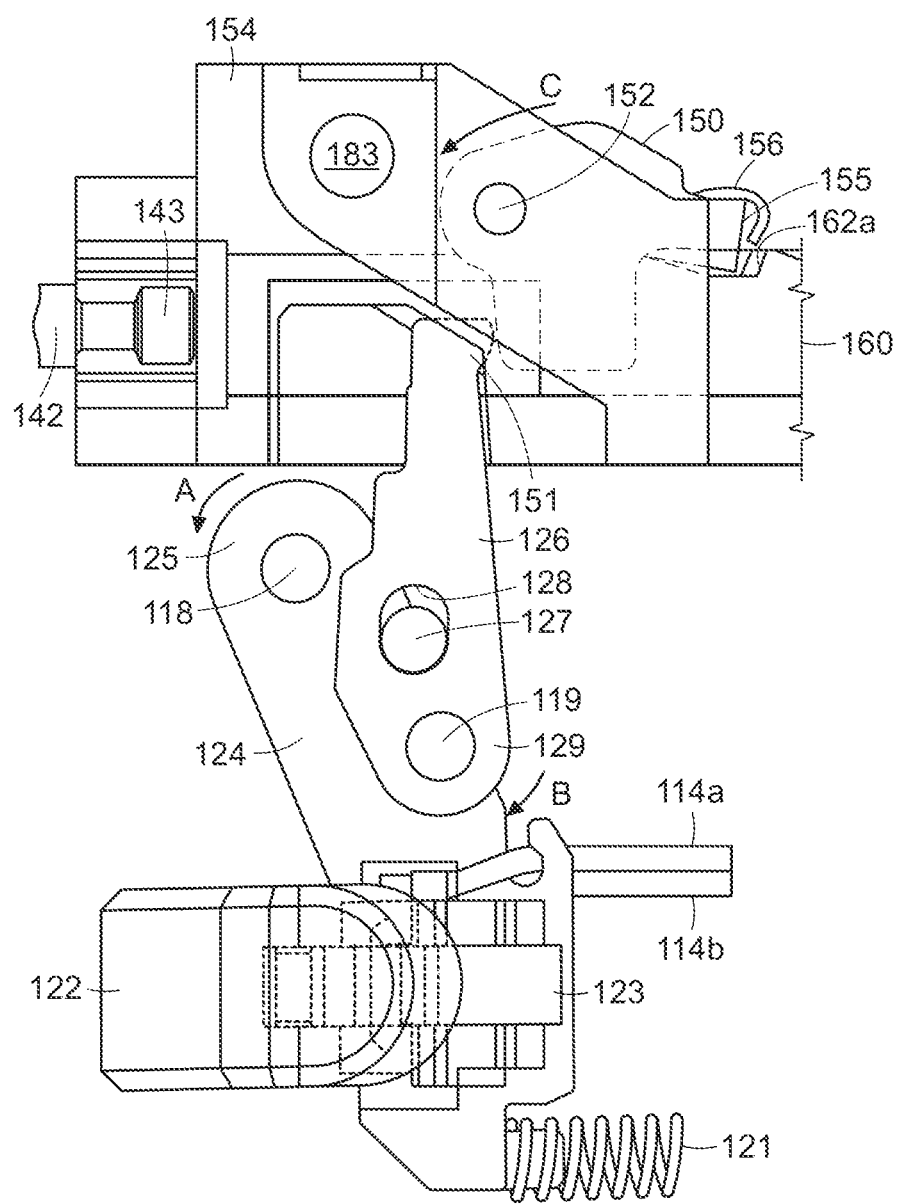
FIG. 32 is an elevational view of the lock system of FIG. 9 in the unactuated, but locked configuration of FIG. 31.
Figure 33:
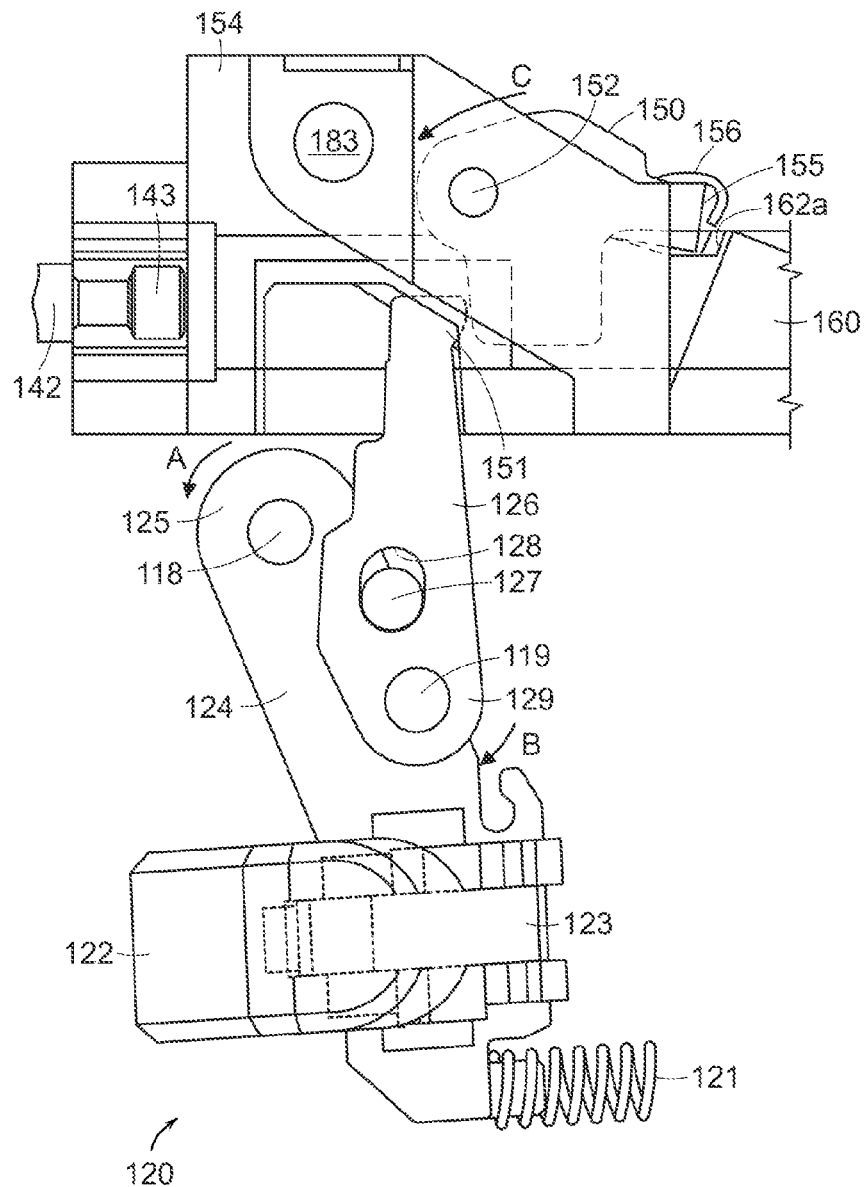
FIG. 33 illustrates the button switch of FIG. 32 in an actuated position.
Figure 34:
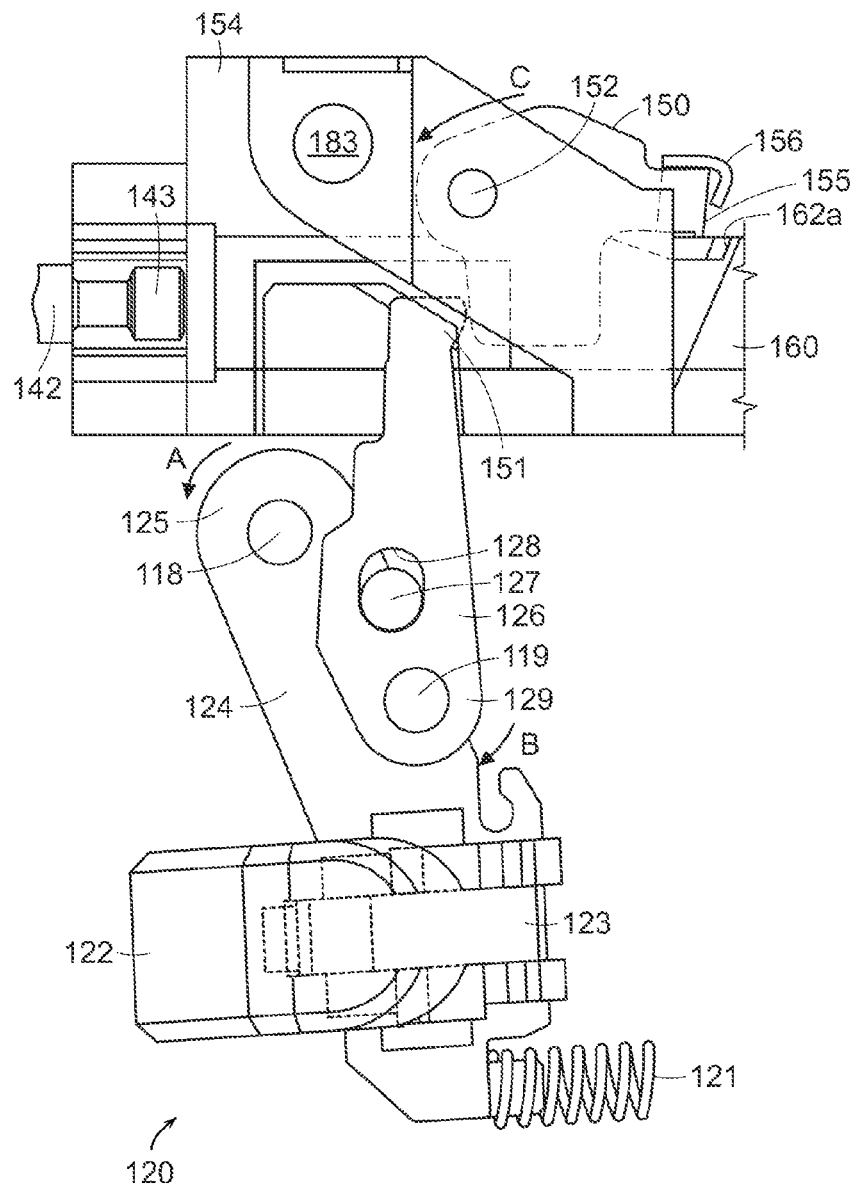
FIG. 34 illustrates the button switch of FIG. 32 in an actuated position, a link of the lock system in an actuated position, and the lock of the lock system in an unlocked position.

In various embodiments, further to the above, the force applied to button 122 in order to actuate switch 123 can cause first link 124 to move. More particularly, the force applied to button 122 can be transmitted through the coil spring to switch 123 wherein the force can then be transferred to first link 124. In at least one embodiment, referring again to FIG. 32, the first link 124 can comprise a first end 125 pivotably mounted to handle body 112 via a pivot or pin 118 extending from handle body 112 and through an aperture in first end 125. When first link 124 is moved by the force, the first link 124 can rotate or pivot about an axis defined by pin 118 in a direction indicated by arrow A (FIG. 32). In various embodiments, the first link 124 can further comprise a drive member 127 extending therefrom which can be configured to move second link 126. In at least one embodiment, the second link 126 can comprise a first end 129 pivotably mounted to handle body 112 via a pivot or pin 119 extending from handle body 112 and through an aperture in first end 129. The drive member 127 can extend into a slot 128 in second link 126 such that, when the first link 124 is rotated about pivot 118 in direction A, the second link 126 can be rotated about pivot 119 in a direction indicated by arrow B (FIG. 32). More particularly, the drive member 127 extending into slot 128 can engage a sidewall of the slot 128 so as to transmit movement between first link 124 and second link 126. In various embodiments, further to the above, the second link 126 can further comprise a second end 151 which can be configured to engage rack 150 and rotate rack lock 150 between an unactuated, locked position (FIG. 33) and an actuated, unlocked position (FIG. 34). More particularly, when second link 126 is rotated in direction B, the rack lock 150 can be rotated in a direction indicated by arrow C (FIG. 32) about an axis defined by pivot 152 on yoke 154. When rack lock 150 is sufficiently rotated in direction C, as described in greater detail further below, tooth 155 extending from rack lock 150 may be sufficiently removed from notch 162a in rack 160 such that rack 160 can be moved relative to lock 150.

As described above, the force applied to button 122 in order to actuate switch 123 can rotate first link 124 about pivot 118, rotate second link 126 about pivot 119, and rotate rack lock 150 between locked and unlocked positions. In at least one embodiment, such a force can be sufficient to actuate switch 123 and unlock rack 150 at the same time, or at least substantially the same time. In such embodiments, energy can be supplied to the electrode 130 at the same time that rack 160 becomes unlocked and capable of advancing knife bar 140 distally within end effector 106 as described in greater detail below. In various circumstances, as a result, the trigger system 120 can assure that the tissue positioned within the end effector is not transected before it is at least partially treated and/or sealed. In various other embodiments, referring again to FIG. 32, the trigger system 120 can further comprise a trigger spring 121 operably engaged with the first link 124, for example, which can be configured to resist the movement of first link 124 in the direction indicated by arrow A. In at least one embodiment, the force applied to button 122 to actuate switch 123 may be insufficient to rotate first link 124 and second link 126 a sufficient distance to move rack lock 150 into its unlocked position. In such embodiments, the switch 123 can be actuated to supply electrode 130 with current while the rack 160 can remain locked in place by rack lock 150. More particularly, further to the above, the tooth 155 of rack lock 150 can remain biased into first notch 162a by lock spring 156 such that rack 160 is prevented from moving, or at least substantially moving, relative to rack lock 150. In various other embodiments, further to the above, a rack lock may be slid between a first position in which it is locked with a rack, such as rack 160, for example, and a second position in which it is unlocked from the rack. In at least one such embodiment, the rack lock can be moved along a straight line.

In order to overcome the biasing force of trigger spring 121, further to the above, a larger, or second, force may need to be applied to button 122 and/or first link 124. More particularly, in the event that the force, or first force, used to depress button 122 and actuate switch 123 is insufficient to unlock rack lock 150, a second, or larger, force can be applied to button 122, for example, in order to sufficiently compress spring 121, sufficiently rotate first link 124 and second link 126, and rotate rack lock 150 into an unlocked position. In such circumstances, a clinician may apply a light force to button 122 in order to actuate the electrical energy system and a heavier force to button 122 in order to unlock the rack 160. In various embodiments, referring to FIG. 1, trigger spring 121 can be positioned intermediate first link 124 and handle body 112 such that trigger spring 121 is compressed as first link 124 is rotated in the direction indicated by arrow A. The length and/or stiffness of trigger spring 121 can be selected such that the coil spring within switch 123 is sufficiently compressed to supply electrode 130 with electrical energy before the trigger spring 121 is sufficiently compressed to unlock rack 160. In such embodiments, as a result, the treatment or sealing of the tissue positioned within the end effector 106, for example, can begin before rack 160 and cutting member 140 can be advanced. In certain circumstances, the difference between the first force and the second force can be large enough such that a surgeon, or other clinician, using the surgical instrument 100 may be provided with a tactile feedback as to whether the surgical instrument is in a first operating condition in which energy is being applied to the tissue and the cutting member is not being advanced within the end effector and a second operating condition in which energy is being applied to the tissue and the cutting member is being advanced within the end effector to transect the tissue. For example, the switch spring and the trigger spring 121 can be selected such that a significantly smaller force is required to depress button 122 and actuate switch 123 as compared to a significantly larger force required to unlock rack lock 150. In the various alternative embodiments where it may be desirable for the electrical energy to be supplied to electrode 130 at the same time, or at least substantially the same time, that the rack 160 becomes unlocked, the stiffness of the spring in switch 123 and the stiffness of trigger spring 121 can be selected such that a force which is sufficient to actuate button 122 can also be sufficient to rotate lock 150 into an unlocked configuration. In at least one such embodiment, the force necessary to actuate button 122 can be the same, or at least substantially the same, as the force necessary to unlock rack 160.

In various circumstances, the surgeon can release button 122 such that the spring of switch 123 can return button 122 to an unactuated position and operably disconnect first portion 114a and second portion 114b of supply wire 114. In such circumstances, electrical current may no longer flow to electrode 130 and, as a result, the electrode 130 and the tissue within the end effector may begin to cool. In addition to the above, the trigger spring 121 may return first link 124 and/or second link 126 to their unactuated positions and the lock spring 156 may return rack lock 150 to an unlocked position. More particularly, referring now to FIG. 36, in the event that the button 122 is released and the rack 160 has not been advanced, or has been returned to its starting position, the lock spring 156 can reposition the lock tooth 155 within the notch 162a and relock the rack 160 in position. In various other circumstances, the rack 160 may be sufficiently advanced such that the rack tooth 155 cannot be reseated within the notch 162a and, as a result, the lock spring 156 may position the tooth 155 against a top surface 161 of rack 160 in an unlocked position. In such circumstances, the rack 160 and the cutting member 140 can be advanced within the tissue without current flowing to the electrode 130. In various other embodiments, referring now to FIG. 35, a rack 160' can comprise a plurality of notches 162a-162e, for example, which can, once the button 122 has been released, allow the lock spring 156 to return the lock 150 to a locked configuration even though the rack 160' and the cutting member 140 have already been advanced. More particularly, depending on the distance that rack 160 has been advanced, the lock spring 156 can position the lock tooth 155 in any one of the notches 162b-162e, for example. In order to prevent the lock 150 from re-engaging with the rack 160' as it is being advanced, in at least one such embodiment, the surgeon may keep the button 122 depressed and the first link 124 and the second link 126 sufficiently rotated in order to keep the lock 150 in an unlocked position. In such circumstances, owing to the constant depression of button 122, electrical energy can be supplied to the electrode 130 during the entire, or at least substantially entire, advancement of rack 160 and cutting member 140.

Figure 34A:
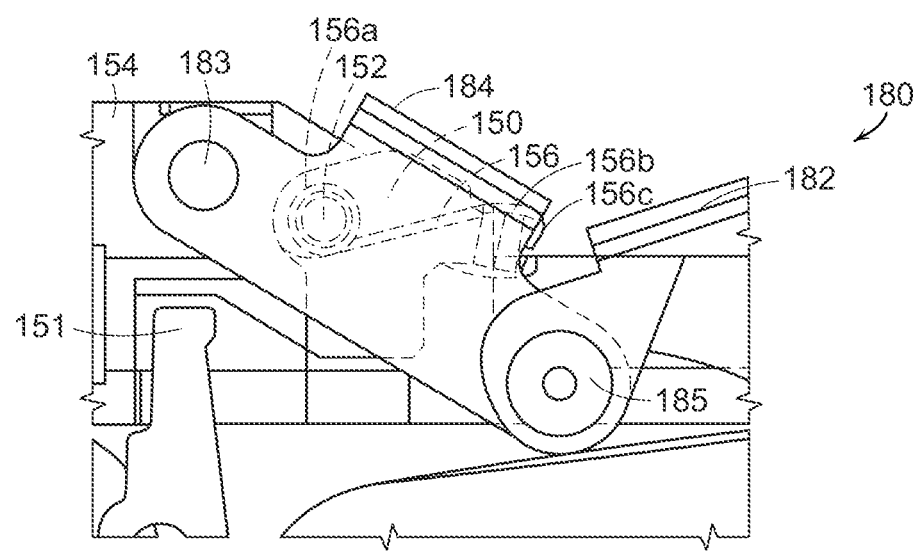
FIG. 34A is a detail view of the lock of FIG. 34 and a lock spring configured to bias the lock into engagement with the rack.
Figure 35:
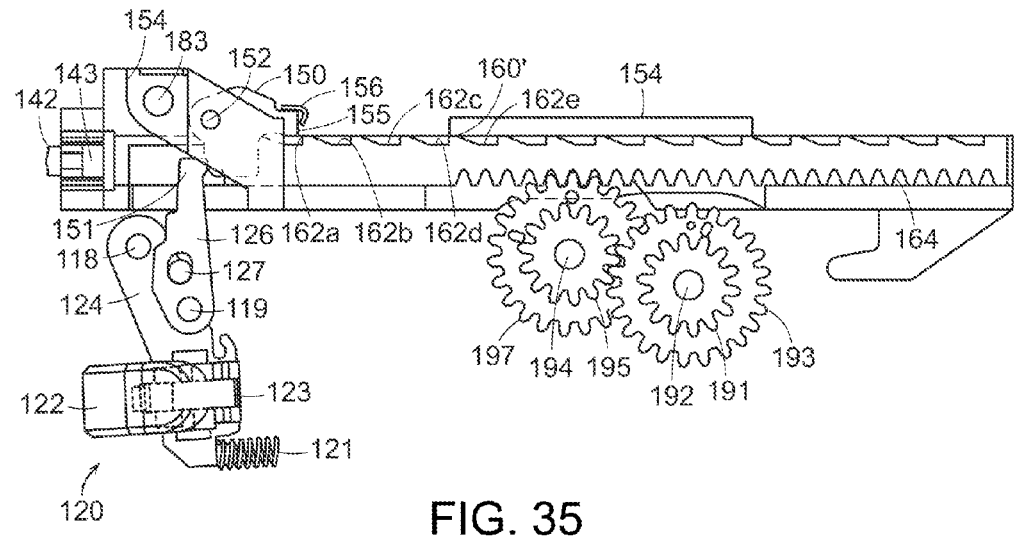
FIG. 35 illustrates the lock system of FIG. 9 in an actuated, unlocked configuration and the rack of FIG. 31 in an unadvanced position.
Figure 36:
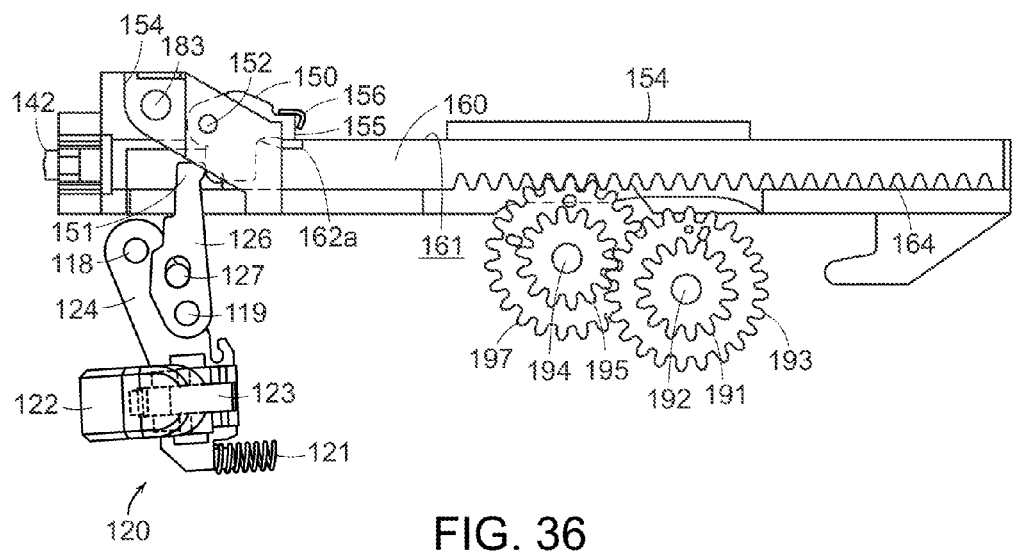
FIG. 36 illustrates the lock system of FIG. 9 in an actuated, unlocked configuration and the rack of FIG. 18 in an unadvanced position.

As discussed above, lock spring 156 can be configured to bias lock 150 into engagement with rack 160. In various embodiments, referring now to FIG. 34A, lock spring 156 can comprise a torsion spring including a coil 156a positioned about pivot pin 152, a first end extending from coil 156a mounted to yoke 154, and a second end 156b. In at least one embodiment, the second end 156b can comprise a torque arm which, when the lock 150 is rotated about pivot pin 152 as described above, the second end 156b can torque or compress the spring coil 156a. In such circumstances, the spring 156 can store potential energy therein which, when released, can act to move lock 150 from its unlocked position into its locked position. In various embodiments, the second end 156b can comprise a hook or attachment portion 156c which can mount the second end 156b to lock 150 such that the second end 156b moves the lock 150.

In various embodiments, referring again to FIGS. 32-34, the distance to move button 122 from an unactuated position to an actuated position can be shorter than the distance to rotate link 124 sufficiently to move lock 150 between a locked position and an unlocked position. Stated another way, in various embodiments, the actuation of button 122, although it may cause first link 124 and second link 126 to rotate, may be insufficient to rotate first link 124 and second link 126 a sufficient distance to move lock 150 into its unlocked configuration. In at least one such embodiment, as a result, the button 122 can be depressed to supply electrical energy to the electrode 130 while the rack 160, for example, can remain locked in position by rack lock 150. In such circumstances, the tissue can be sealed, or at least partially sealed, before the cutting member 140 is advanced through the tissue within the end effector 106. In various circumstances, the button 122 and the first link 124 can be moved an additional distance in order to sufficiently rotate lock 150 into an unlocked configuration such that rack 160 and cutting member 140 can be advanced into and/or through the tissue. Stated another way, in various embodiments, the button 122 can be moved a first distance to supply electrical current to electrode 130 although the button 122 can be moved a total distance which is greater than the first distance to unlock rack lock 150. In various embodiments, the difference between the first distance and the total distance that button 122 is moved can be sufficient to provide a sufficiently large window of operation to allow the surgeon to move button 122 within a range of distances while not unlocking the rack lock 150. In the various alternative embodiments where it may desired to supply electrical energy to electrode 130 at the same time, or at least substantially the same time, that rack 160 becomes unlocked, the distance necessary to actuate button 122 may the same, or at least substantially the same, as the distance necessary to move lock 150 between its locked and unlocked configurations.

Figure 18:
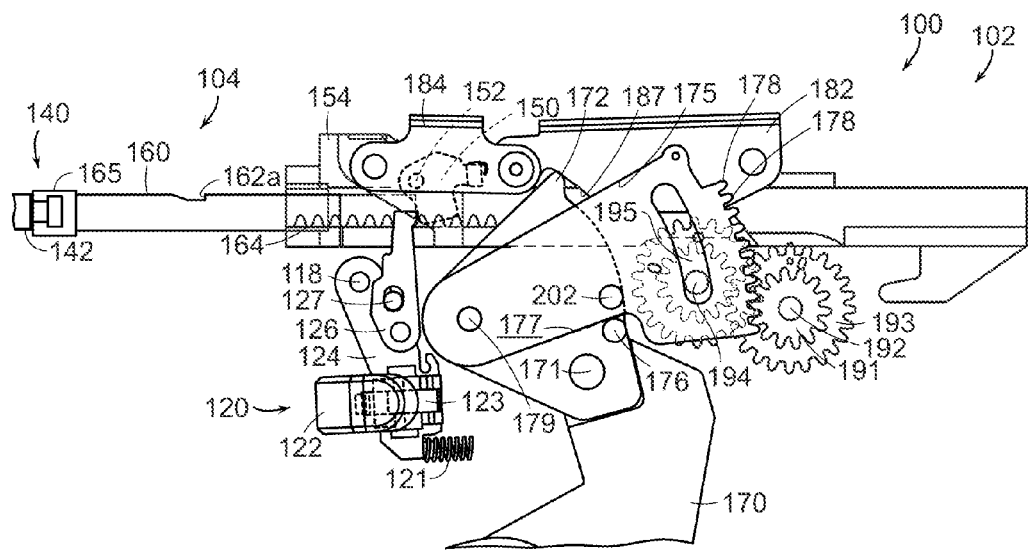
FIG. 18 illustrates the trigger of FIG. 4 in a fully actuated position and a rack of the second drive system of FIG. 15 in a fully advanced position.

Once rack lock 150 has been disengaged from rack 160, as described above, rack 160 and cutting member 140 can be advanced toward distal end 107 (FIG. 3) of end effector 106. In various embodiments, as described in greater detail below, the advancement of cutting member 140 can, one, move jaw 108 toward jaw 109 and, two, incise the tissue captured between jaw 108 and jaw 109. Referring to FIG. 1, the handle 102 can further comprise a trigger 170 which can be moved between an unactuated position, as illustrated in FIG. 1, and an actuated position, as illustrated in FIG. 18. The movement of trigger 170 between its actuated position and unactuated position can define one stroke of trigger 170, although such a stroke can comprise two different ranges of motion. More particularly, in at least one embodiment, the stroke can comprise a first range of motion which drives a first drive system and a second range of motion which drives a second drive system. In various embodiments, the trigger 170, in co-operation with the first drive system, can advance the rack 160 and the cutting member 140 between a first position (FIG. 3) and a second position (FIG. 7) during the first range of motion of trigger 170, wherein the trigger 170, in co-operation with the second drive system, can advance the rack 160 and the cutting member 140 between a second position (FIG. 7) and a third position (FIG. 19) during the second range of motion of trigger 170. When the cutting member 140 is moved between its first position (FIG. 3) and its second position (FIG. 7), as described in greater detail below, the cutting member 140 can move the second jaw 108 toward the first jaw 109 and clamp tissue positioned therebetween. When the cutting member 140 is moved between its second position (FIG. 7) and its third position (FIG. 19), as described in greater detail further below, the cutting member 140 can be advanced toward the distal end 107 to incise the tissue clamped between jaw 108 and jaw 109.

Figure 2:
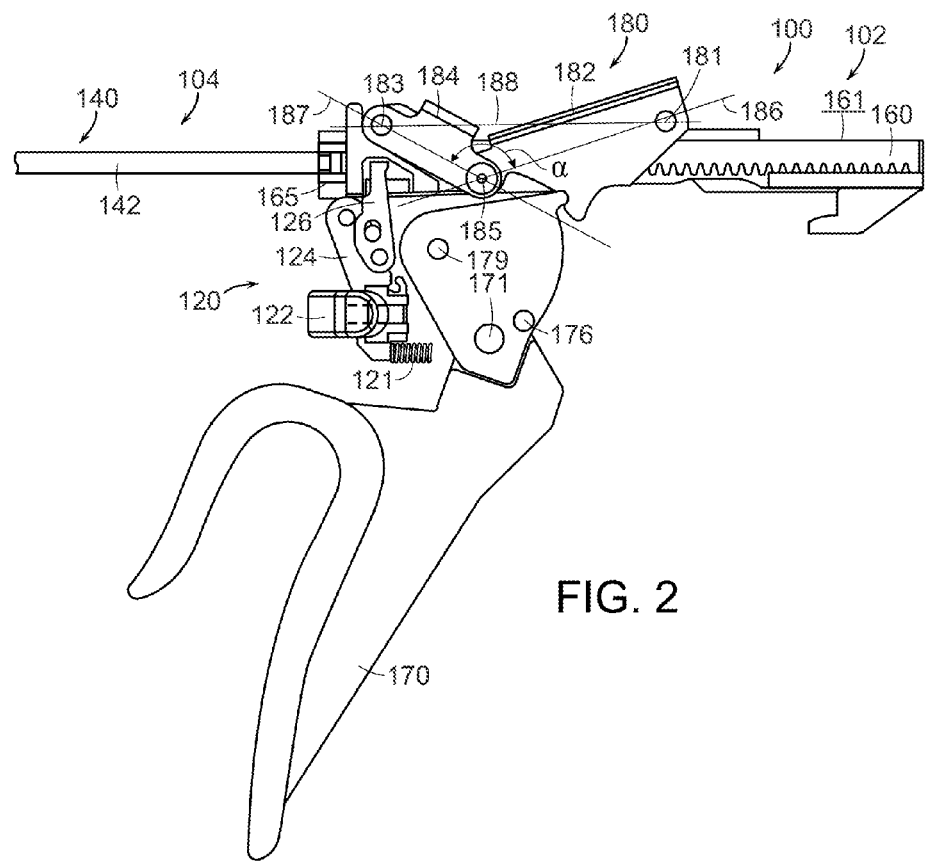
FIG. 2 illustrates the handle of FIG. 1 in an unactuated configuration with various components removed.

In various embodiments, referring now to FIG. 2, the first drive system can comprise a toggle clamp 180 which can be moved between a first configuration (FIG. 2) associated with the first position (FIG. 3) of cutting member 140 and a second configuration (FIG. 6) associated with the second position (FIG. 7) of cutting member 140. The toggle clamp 180, referring again to FIG. 2, can comprise a first link 182 and a second link 184. The first link 182 can comprise a first end pivotably mounted to handle body 112 at first pivot 181, via a pivot pin, for example, and, in addition, the second link 184 can comprise a first end pivotably mounted to yoke 154 at a second pivot 183, also via a pivot pin, for example. Further to the above, the first link 182 and the second link 184 can each comprise second ends which are pivotably mounted to each other via an intermediate pivot pin 185, for example. In certain embodiments, the intermediate pivot pin 185 can comprise a vertex of an angle defined between a first line, or axis, 186 extending through the centers of first pivot 181 and intermediate pivot 185 and a second line, or axis, 187 extending through the centers of second pivot 183 and intermediate pivot 185. In various embodiments, the first line 186 and the second line 187 can define a vertex angle $\alpha$ therebetween. Opposite vertex angle $\alpha$ is a line, or axis, 188 defined between the center of first pivot 181 and the center of second pivot 183. When toggle clamp 180 is in its first configuration, in various embodiments, the vertex angle $\alpha$ can be about 90 degrees and/or slightly greater than 90 degrees, for example. In at least one embodiment, angle $\alpha$ can be about 120 degrees when toggle clamp 180 is in its first configuration, for example. Although such angles may be suitable in various circumstances, any other suitable angle can be used.

Figure 4:
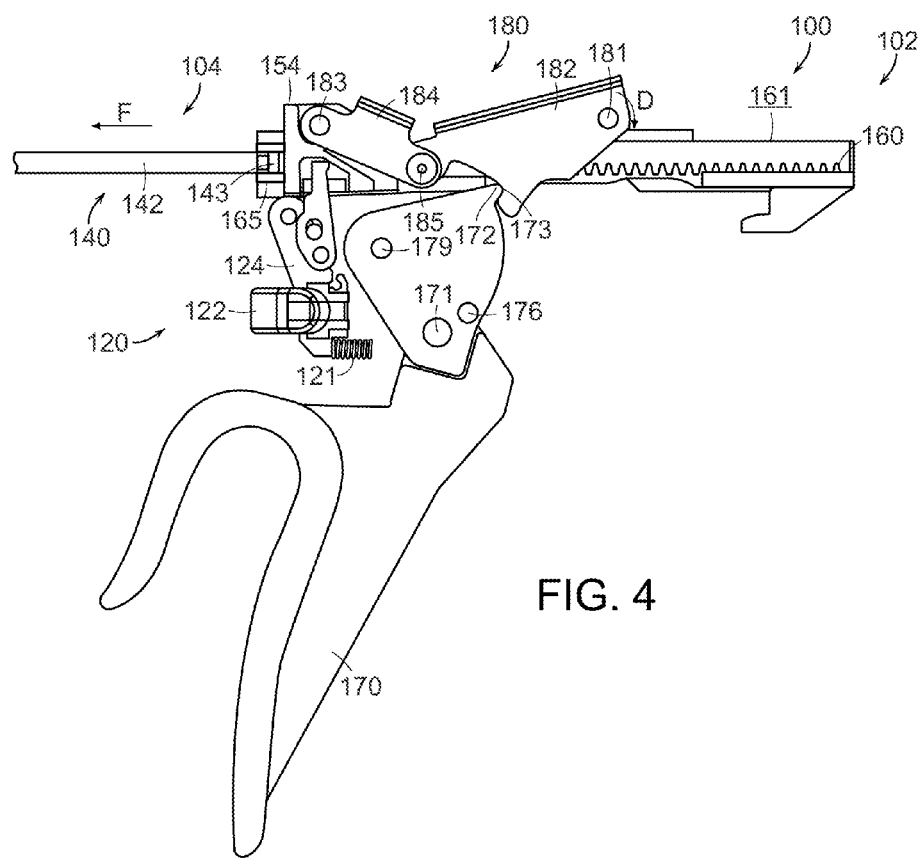
FIG. 4 illustrates a trigger and a first drive system of the handle of FIG. 2 in a partially actuated configuration.
Figure 6:
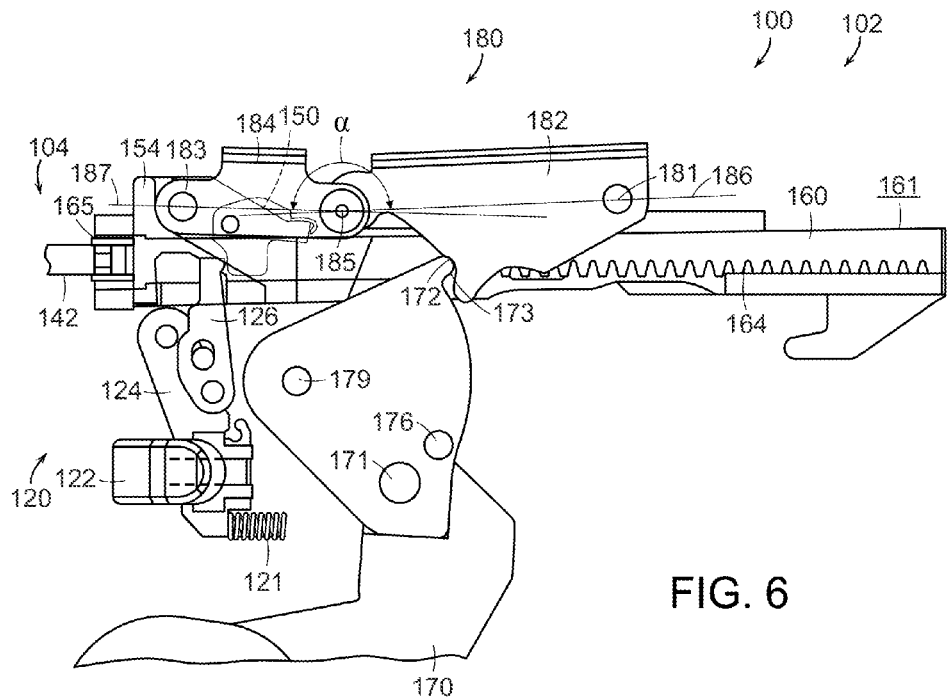
FIG. 6 illustrates a toggle clamp of the first drive system of FIG. 4 in a completely actuated configuration.

In various embodiments, further to the above, the trigger 170 can be moved from its unactuated position (FIG. 2) into a partially actuated position (FIG. 4) as part of its first range of motion. As the reader will see when comparing FIG. 2 and FIG. 4, trigger 170 is pivotably mounted to handle body 112 via a pivot 171, such as a pivot pin, for example. When trigger 170 is rotated about pivot 171, trigger 170 can begin to move the toggle clamp 180 from its first configuration (FIG. 2) into its second configuration (FIG. 6). More particularly, in at least one embodiment, the trigger 170 can further comprise a cam, or driver, 172 extending therefrom which can be configured to engage first link 182 and lift the second end of link 182 upwardly and, at the same time, rotate first link 182 about first pivot 181 in a direction indicated by arrow D (FIG. 4). Owing to the pivoted connection of the second ends of first link 182 and second link 184, the upward movement of the second end of first link 182 can cause the second end of second link 184 to move upwardly and, at the same time, rotate about second pivot 183 in a direction indicated by arrow E (FIG. 4). In various embodiments, the first link 182 can comprise a cam, or drive, pocket 173 which can be engaged by cam, or driver, 172 in order to transmit the rotation of trigger 170 to first link 182. In order to accommodate the upward movement of the second ends of links 182 and 184 and the upward movement of intermediate pivot 185, the yoke 154 can translate distally in a direction indicated by arrow F (FIG. 4).

Figure 5:
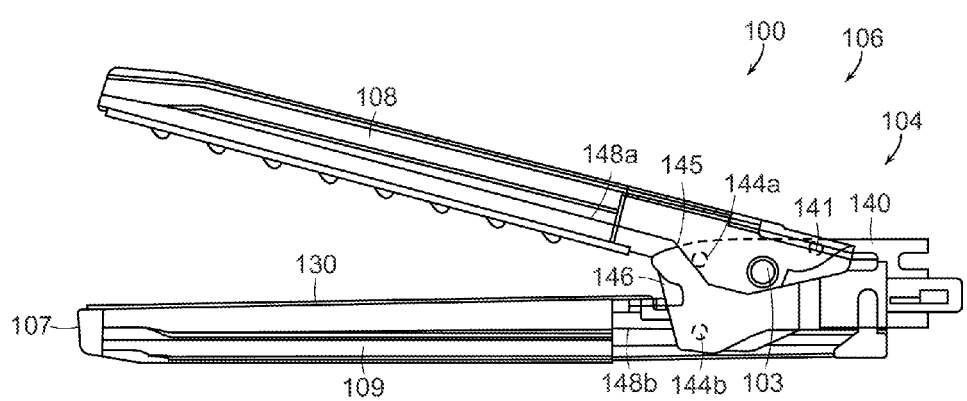
FIG. 5 is an elevational view of the end effector of FIG. 3 illustrated in a partially closed configuration and the knife bar of FIG. 3 in a partially advanced position.

In various embodiments, referring again to FIG. 4, the distal movement of yoke 154 in the direction F can be transmitted to rack 160 and cutting member 140 such that rack 160 and cutting member 140 are also moved in direction F. More particularly, further to the above, the rack lock 150 mounted to yoke 154, when engaged with rack 160, can allow the yoke 154 to pull the rack 160 distally when the yoke 154 is pushed distally by toggle clamp 180 as described above. Furthermore, owing to the connection between rack 160 and cutting member 140, the distal movement of rack 160 can be transmitted to cutting member 140. More particularly, in at least one embodiment, the cutting member 140 can comprise a proximal portion 142 which can be connected to the distal end 165 of rack 160. In various embodiments, such a connection can prevent, or at least inhibit, relative longitudinal movement between cutting member proximal end 142 and rack distal end 165 while permitting relative rotational movement therebetween owing to a round head 143 of the proximal end 142 captured within a round cavity in the distal end 165 of rack 160. In any event, referring now to FIG. 5, the proximal movement of cutting member 140 can, in at least one embodiment, cause cutting member 140 to engage the second jaw 108 and move, or rotate, second jaw 108 toward first jaw 109. More particularly, the cutting member 140 can comprise one or more cams, or cam pins, 144a which can be configured to engage one or more cam surfaces 145 on second jaw 108 and rotate second jaw 108 downwardly about one or more pivot pins 103, for example.

Figure 7:
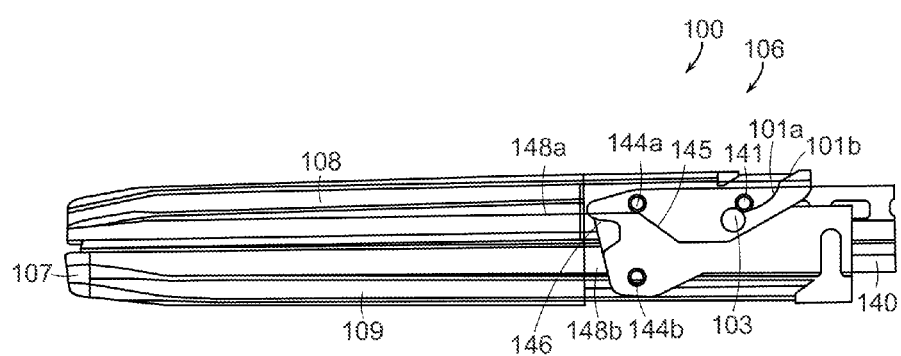
FIG. 7 is an elevational view of the end effector of FIG. 3 illustrated in a fully closed configuration and the knife bar in a partially advanced position.

In various embodiments, further to the above, the rotation of trigger 170 through its first range of motion can move the toggle clamp 180 between its first, or unactuated, configuration (FIG. 2) and its second, or fully actuated, configuration (FIG. 6). Also further to the above, the movement of the toggle clamp 180 between its first configuration and its second configuration can move the cutting member 140 between its first position (FIG. 3) and its second position (FIG. 7) and, as a result, move second jaw 108 between its fully open position (FIG. 3) and its fully closed position (FIG. 7). When comparing the toggle clamp 180 in its second configuration as compared to its first configuration, the reader will note that the vertex angle α defined between first line 186 and second line 187 is about 180 degrees, for example. In at least one embodiment, the vertex angle α can be about 175 degrees, for example. Furthermore, the reader will note that the second pivot 183 has moved distally respect to first pivot 181 as yoke 154 has been moved distally as described above. As a result of the above, the toggle clamp 180 can transmit a very large longitudinal force to rack 160 and cutting member 140 in the distal direction F. In fact, this very large longitudinal force can increase exponentially and/or asymptotically as the vertex angle α approaches approximately 180 degrees. This very large longitudinal force can apply a large biasing force to second jaw 108 such that a large clamping force, or pressure, is applied to the tissue positioned intermediate the first jaw 109 and the second jaw 108.

Figure 8:
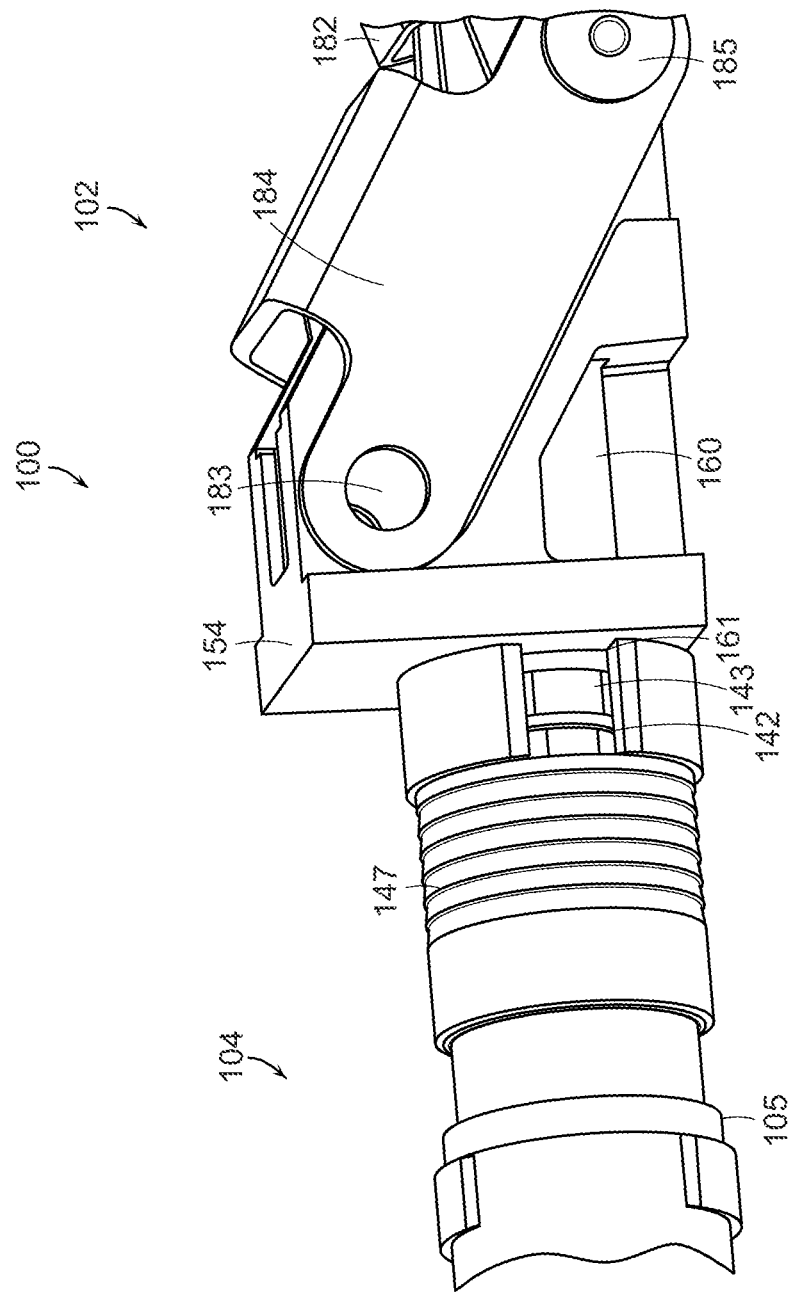
FIG. 8 is a detail view of a yoke spring positioned intermediate a shaft of the surgical instrument of FIG. 1 and a yoke of the first drive system of FIG. 4.

In various embodiments, referring now to FIG. 8, the distal movement of yoke 154 can compress a yoke spring, such as axial spring 147, for example, intermediate yoke 154 and a spine 105 of shaft 104. In at least one embodiment, as described in greater detail below, the axial spring 147 can store potential energy therein which can be released in order to at least partially retract rack 160 and cutting member 140. Although the toggle clamp 180 is illustrated in its first, or unactuated configuration, in FIG. 8, the axial spring 147 is at least partially compressed between shaft spine 105 and yoke 154. In various circumstances, the compression force applied to shaft spine 105 and yoke 154 by spring 147 can provide an additional benefit of inhibiting relative movement between shaft spine 105 and yoke 154.

Figure 9:
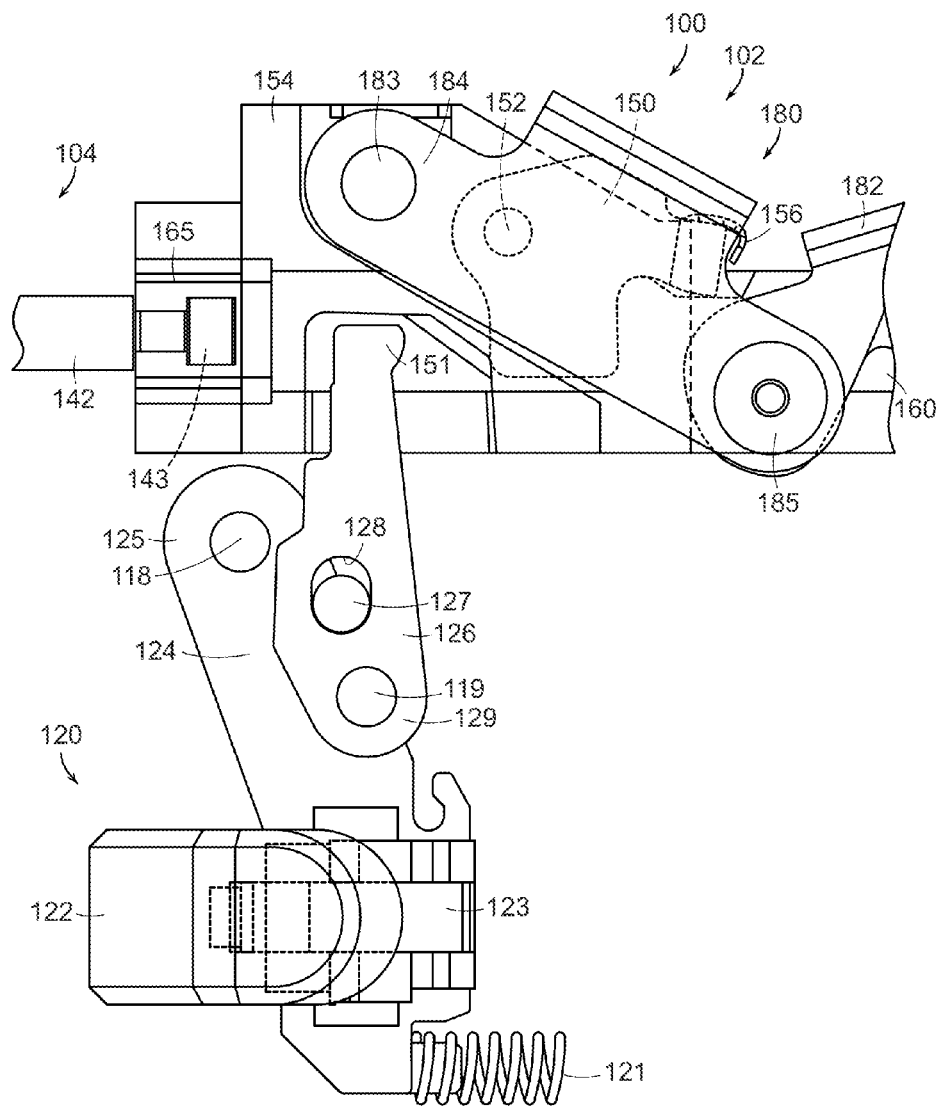
FIG. 9 illustrates a lock system for locking and unlocking a second drive system of the handle of FIG. 2, wherein the lock system is illustrated in an unactuated and locked configuration.
Figure 10:
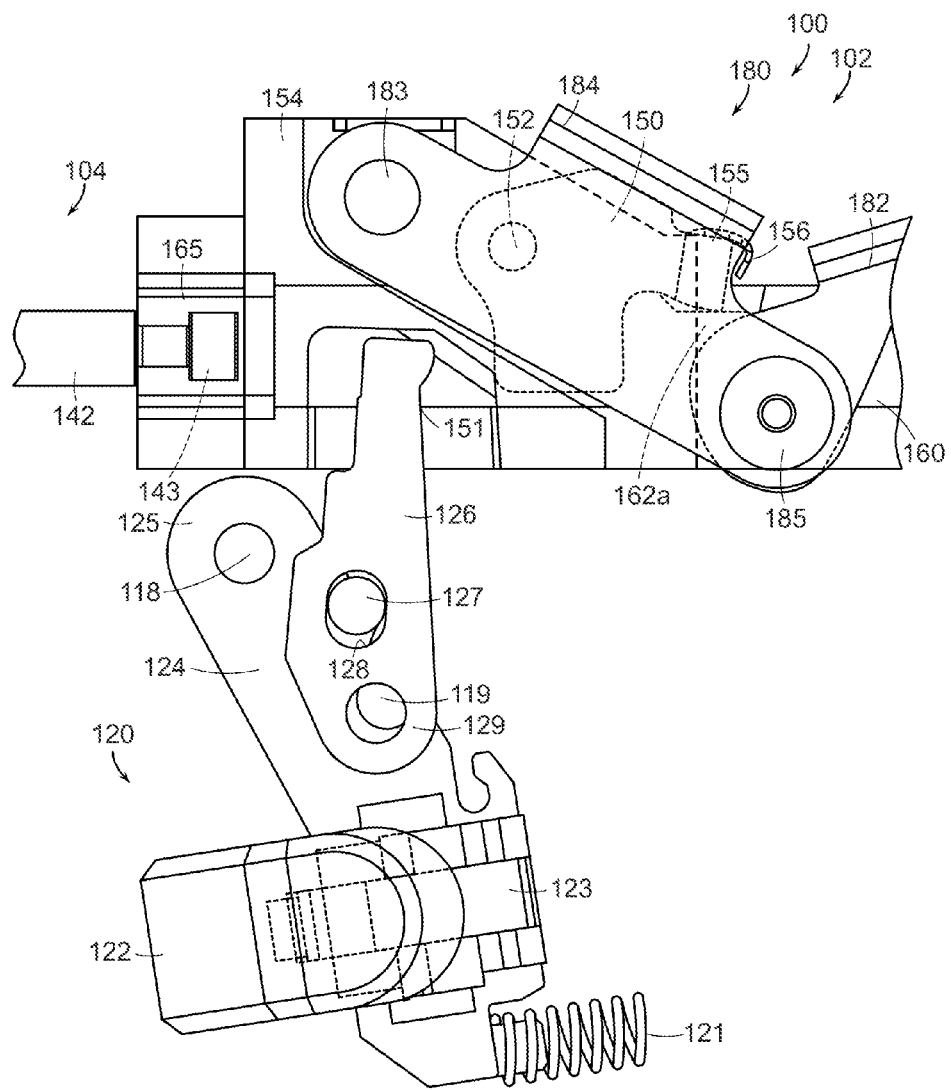
FIG. 10 illustrates the lock system of FIG. 9 in an actuated, but locked configuration and the first drive system of FIG. 4 in an unactuated configuration.
Figure 11:
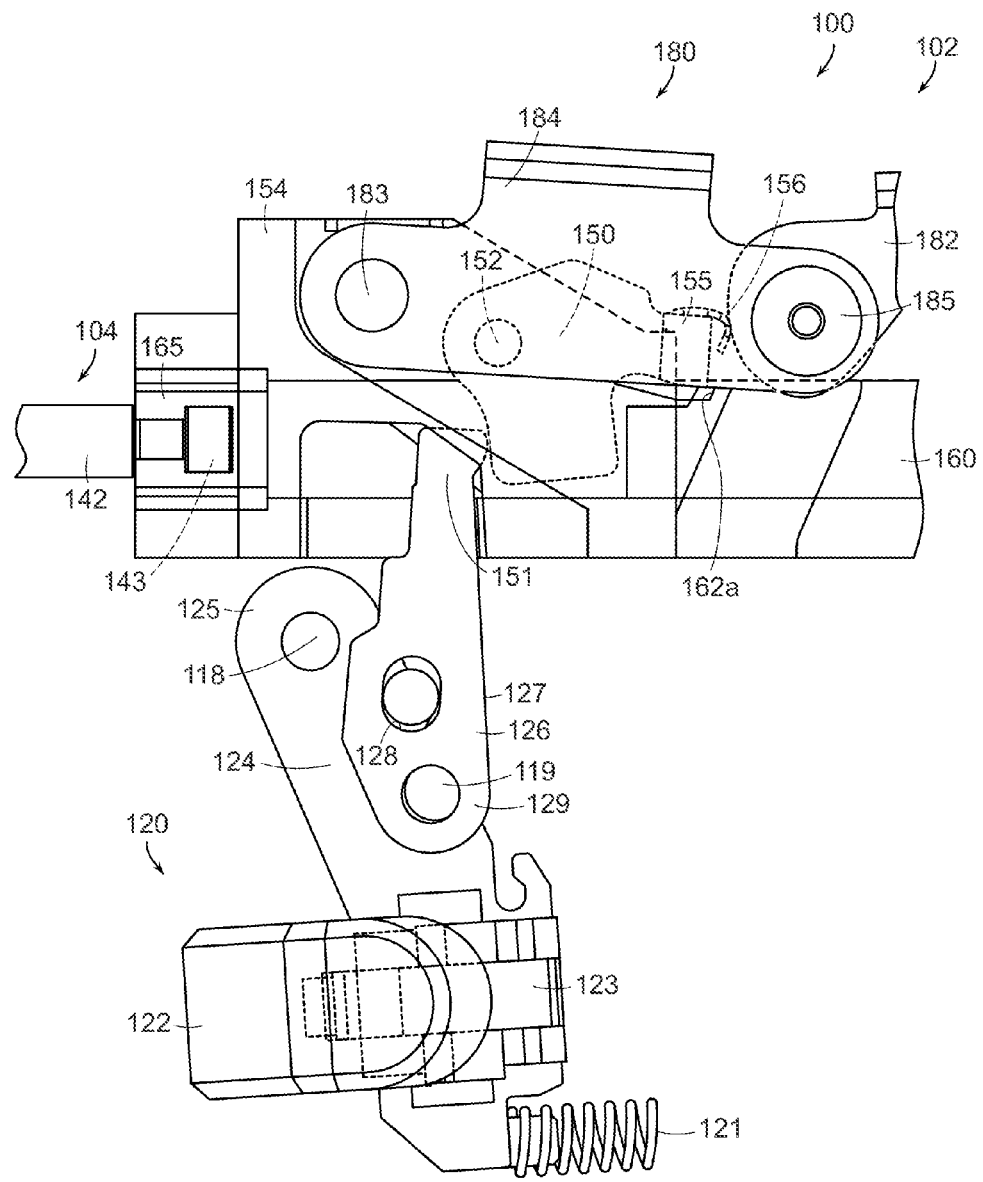
FIG. 11 illustrates the lock system of FIG. 9 in an actuated and unlocked configuration and the first drive system of FIG. 4 in an actuated configuration.
Figure 12:
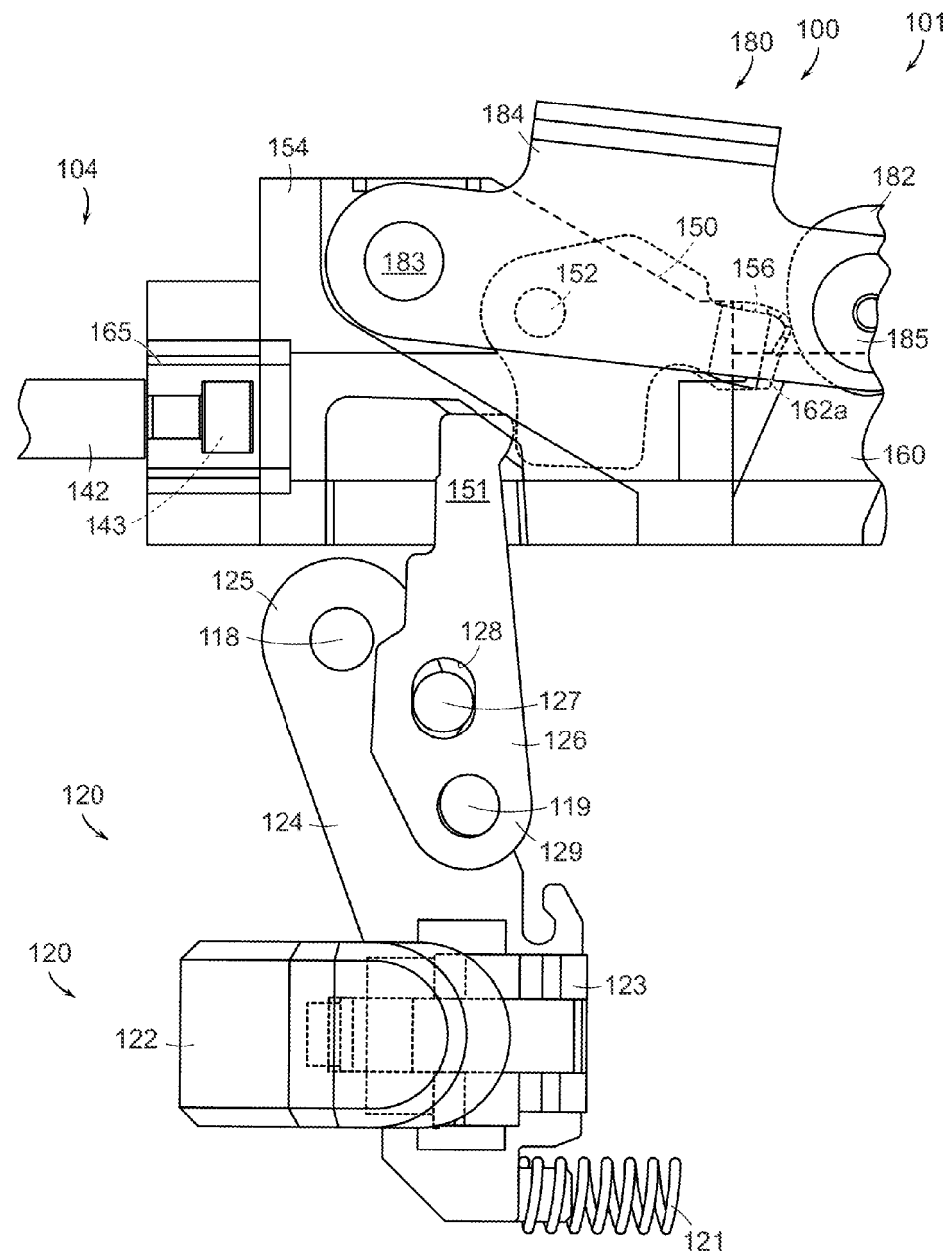
FIG. 12 illustrates the lock system of FIG. 9 in an unactuated and locked configuration and the first drive system of FIG. 4 in an actuated configuration.
Figure 13:
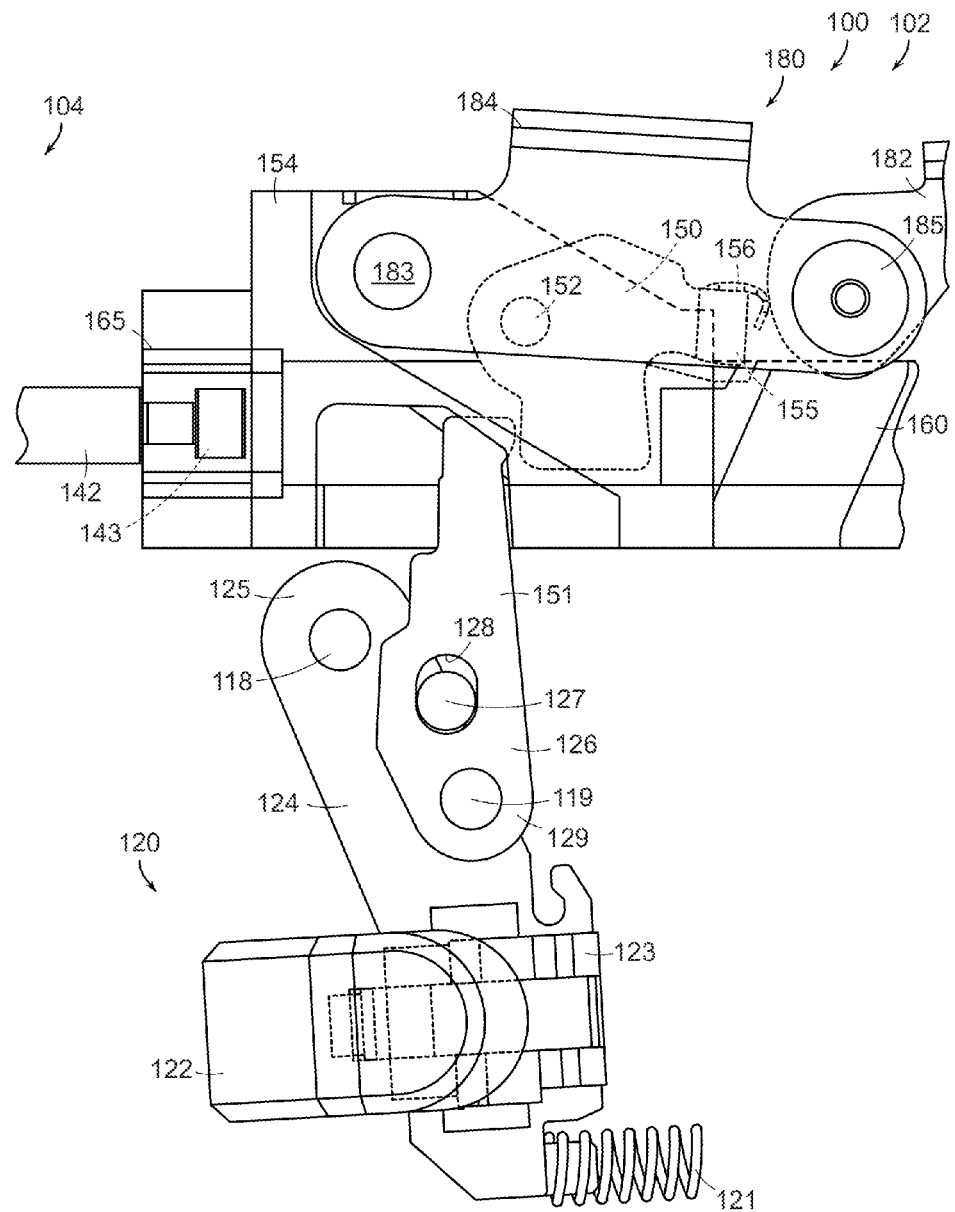
FIG. 13 illustrates the lock system of FIG. 9 in an actuated and unlocked configuration and the first drive system of FIG. 4 in an actuated configuration.
Figure 14:
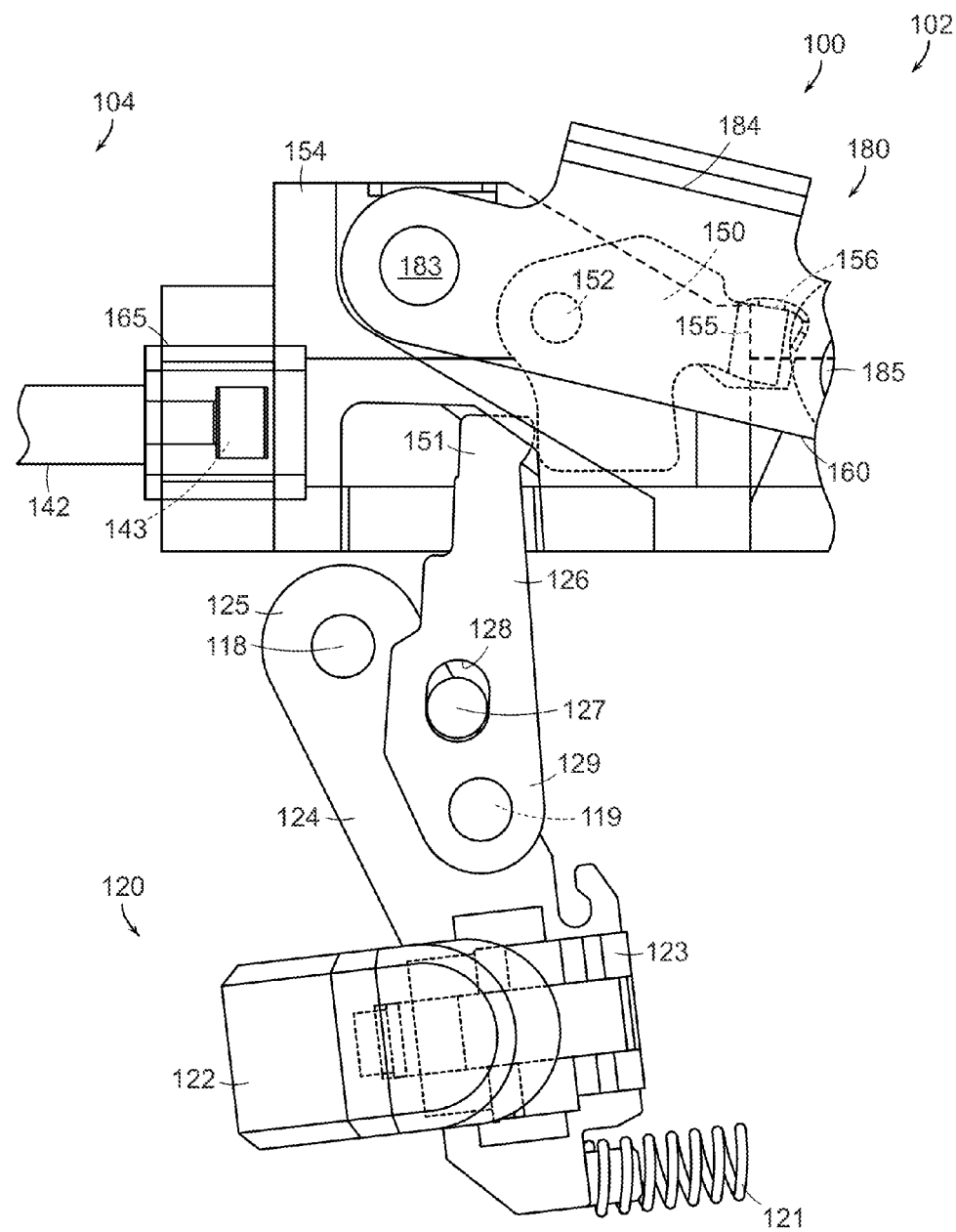
FIG. 14 illustrates the lock system of FIG. 9 returned to a locked configuration.

In various embodiments, referring now to FIG. 9 which illustrates the toggle clamp 180 in its first configuration and the trigger assembly 120 in its unactuated configuration, the rack lock 150 is in its locked position and rack 160 is in its unadvanced position. In such a configuration, further to the above and referring now to FIG. 10, the trigger assembly 120 can be actuated so as to rotate first link 124 about pivot 118 and rotate second link 126 about pivot 119; however, in circumstances where the rack 160 and cutting member have not yet been advanced into their second positions, for example, the actuation of trigger assembly 120 may not move rack lock 150 into its unlocked position. Upon the advancement of rack 160 and cutting member 140 into their second positions, referring now to FIG. 11, the rack lock 150 can be moved into contact with second link 126 such that rack lock 150 is rotated from its locked position to its unlocked position. Alternatively, referring now to FIG. 12, the rack 160 and cutting member 140 can be advanced from their first positions (FIG. 9) to their second positions (FIG. 12) when the toggle clamp 180 is moved from its first configuration into its second configuration, as described above, and wherein, upon a sufficient actuation of trigger assembly 120, as described above, the second link 126 can contact rack lock 150 and rotate rack lock 150 into its unlocked configuration as illustrated in FIG. 13. In any event, upon the completion of its first range of motion, trigger 170 can, as described in greater detail below, become operably disengaged from the first drive system and/or operably engaged with the second drive system.

Figure 15:
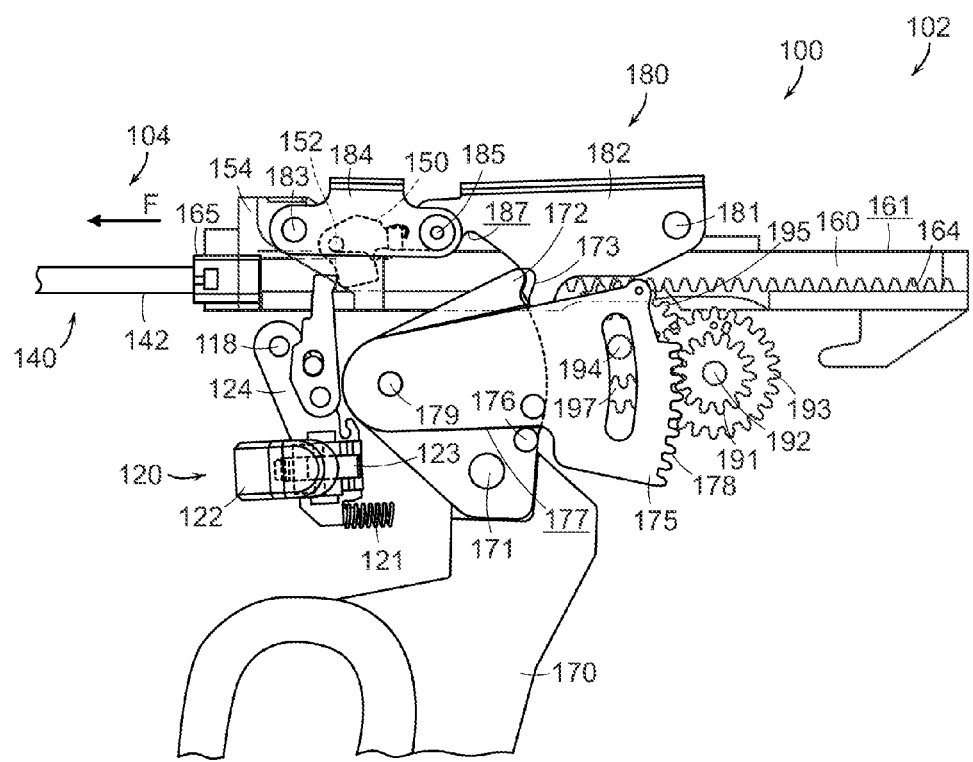
FIG. 15 illustrates the toggle clamp of the first drive system in a completely actuated configuration and the trigger of FIG. 4 operably engaged with a second drive system.

Referring now to FIG. 15 which depicts the trigger 170 at the end of its first range of motion, the reader will see that the cam 172 is no longer positioned within pocket 173 in first link 182. As a result, the cam 172 may no longer drive the toggle clamp 180 despite any further rotation of trigger 170 toward its actuated position (FIG. 18), and, as a result, the trigger 170 may be operably disconnected from the first drive system. The reader will also see that, at this position of trigger 170, the trigger 170 has been moved into operative engagement with trigger gear 175 and the second drive system. More particularly, referring now to FIG. 16, the trigger 170 can further comprise a drive pin 176 extending therefrom which is configured to contact the bottom surface 177 of trigger gear 175 and, once engaged with trigger gear 175, push, or rotate, the trigger gear 175 upwardly such that the trigger gear 175 rotates a compounding gear 191 of the rack and pinion system 190 as trigger 170 is moved through its second range of motion. As the reader will note, the trigger gear 175 comprises an array of teeth 178 which are operably engaged with, or meshed with, the compounding gear 191 while the trigger 170 is moved through its first range of motion, although, the teeth 178 do not drive the compounding gear 191 during the first range of motion of trigger 170. On the other hand, the rotation of trigger 170 in its second range of motion can cause trigger gear 175 to drive or rotate compounding gear 191 as described in greater detail further below. In various embodiments, further to the above, the disengagement of cam 172 from pocket 173 in first link 182 can occur at the same time, or at least substantially the same time, as the trigger 170 comes into operative engagement with trigger gear 175. Alternatively, the trigger 170 may not come into operative engagement with trigger gear 175 until after the cam 172 has been disengaged from pocket 173. In at least one such embodiment, the rotation of trigger 170 may comprise a dwell period in which the trigger 170 is not operatively engaged with either the first drive system of the second drive system.

Figure 16:
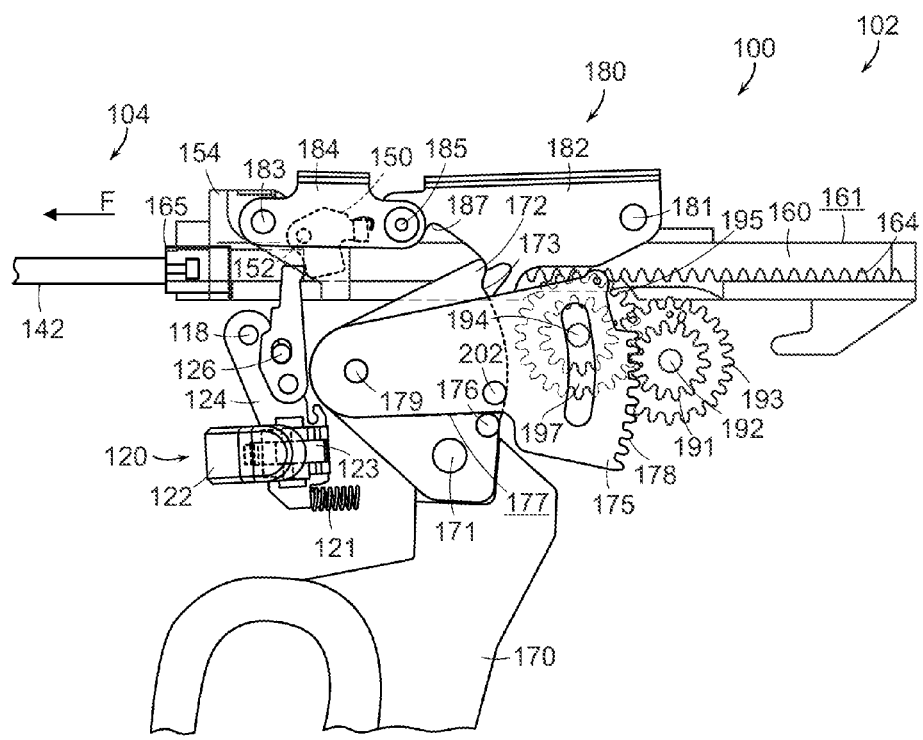
FIG. 16 illustrates a trigger gear portion of the trigger of FIG. 4 operably engaged with a compound gear system of the second drive system.

Once trigger 170 has been operatively engaged with trigger gear 175, further to the above, the further rotation of trigger 170 can, one, cause the cam 172 to move relative to a bottom surface 187 of first link 182, and, two, rotate compounding gear 191. In at least one embodiment, the compounding gear 191 can be mounted to a pin 192 which can be rotatably mounted between the two halves of handle body 112. Referring again to FIG. 16, the rack and pinion system 190 can further comprise an additional, or second, compounding gear 193 which can be mounted to pin 192. In at least one such embodiment, the compounding gears 191, 193 can be mounted to pin 192 such that the rotation of one of compounding gears 191, 193 causes the rotation of the other of the compounding gears 191, 193. In various embodiments, the rack and pinion system 190 can further comprise a third compounding gear 195 which can be mounted to a pin 194 which can be rotatably mounted between the two halves of handle body 112. As illustrated in FIG. 16, the third compounding gear 195 can be operably meshed with the second compounding gear 193 such that the rotation of second compounding gear 193 can rotate the third compounding gear 195. The rack and pinion system 190 can further comprise a pinion gear 197 which can also be mounted to pin 194, wherein, similar to the above, the compounding gear 195 and the pinion gear 197 can be mounted to pin 194 such that the rotation of one of gears 195, 197 causes the rotation of the other of the gears 195, 197. As also illustrated in FIG. 16, the pinion gear 197 is operably or meshingly engaged with the rack teeth 164 on rack 160 such that the rotation of pinion gear 197 can move, or displace, rack 160 along a straight, or at least substantially straight, path, for example.

Figure 17:
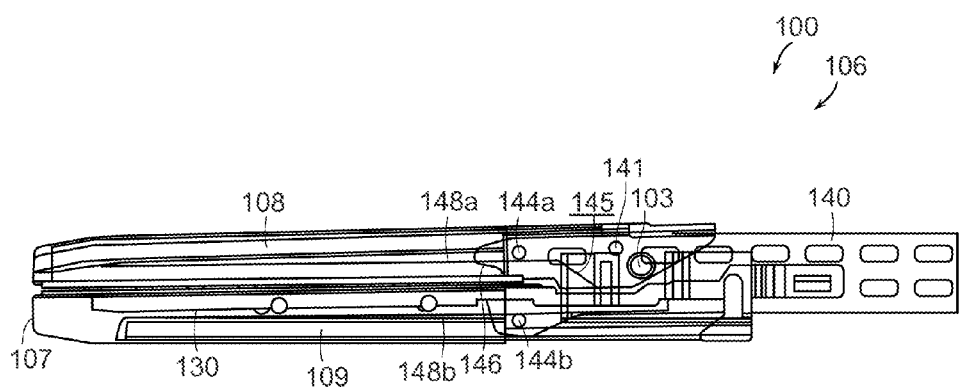
FIG. 17 illustrates the end effector of FIG. 3 in a fully closed position and the knife bar of FIG. 3 in a partially advanced position.
Figure 19:
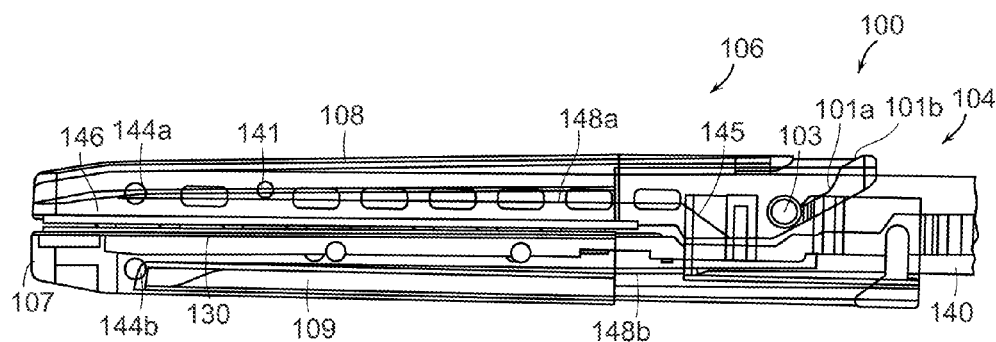
FIG. 19 illustrates the end effector of FIG. 3 in a fully closed position and the knife bar of FIG. 3 in a fully advanced position proximal to a distal end of the end effector.
Figure 20:
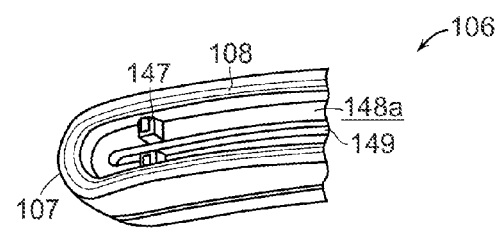
FIG. 20 is a detail view of the distal end of the end effector of FIG. 19.

During the second range of motion of trigger 170, further to the above, the rotation of trigger 170 can be transmitted to pinion gear 197 via compounding gears 191, 193, and 195 such that, owing to the gear ratio of gears 191, 193, 195, and 197, a small rotation of trigger 170 can result in a large displacement of rack 160 and cutting member 140. In various embodiments, as described above, the rotation of trigger 170 through its second range of motion can move cutting member 140 between its second position (FIG. 17) and its third position (FIG. 19). In its second position, referring to FIG. 17, the cutting member 140 can be positioned within the end effector 106 such that the knife edge 146 of cutting member 140 is positioned to be advanced through the tissue captured between first jaw 109 and second jaw 108, and owing to the rotation of trigger 170, trigger gear 175, and gears 191, 193, 195, and 197, the rack 160 can be displaced in the distal direction F so as to displace the cutting member 140 toward the distal end 107 of end effector 106. In its third position, referring to FIGS. 18 and 19, the cutting member 140 can be positioned at the distal end 107 of end effector 106. In at least one embodiment, referring to FIG. 20, jaw 108 and/or jaw 109 can comprise a slot 149 which can be configured to receive at least a portion of cutting member 140 and guide cutting member 140 toward the distal end 107. In certain embodiments, the cam pins 144a extending from cutting member 140 can be configured to ride on top of cam surface 148a on the outside of jaw 108 such that jaw 108 is compressed toward jaw 109. Similarly, cutting member 140 can further comprise cam pins 144b extending therefrom which can be configured to ride on cam surface 148b on the outside of jaw 109 such that jaw 109 is compressed toward jaw 108. Stated another way, the cam pins 144a and 144b can engage the cam surfaces 148a and 148b, respectively, in order to apply a clamping force or pressure to the tissue positioned intermediate jaw 108 and jaw 109. In certain embodiments, referring again to FIG. 20, jaw 108 and/or jaw 109 can further comprise a stop 147 which can be configured to stop the distal displacement of cutting member 140 through the tissue. In at least one embodiment, the stop 147 can be positioned proximally with respect to the distal end of electrode 130 such that the knife edge 146 may not transect tissue which has not been sealed.

Figure 21:
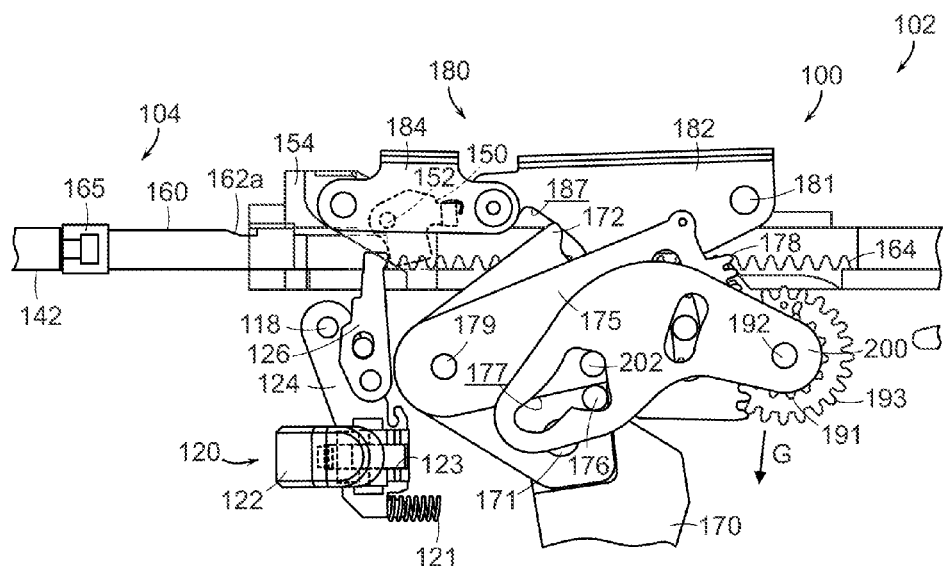
FIG. 21 illustrates a return plate of the handle of FIG. 2 operably engaged with the trigger gear of FIG. 16.
Figure 22:
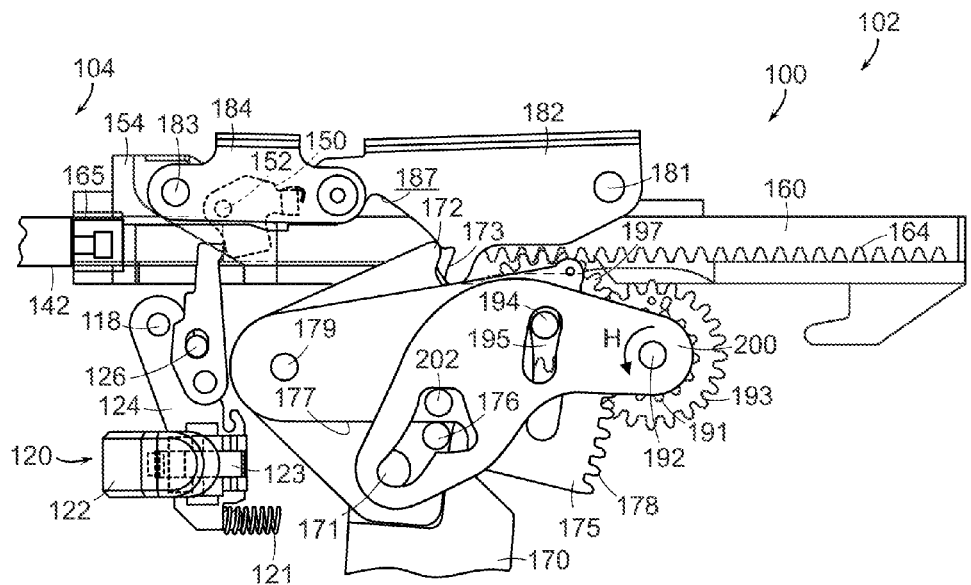
FIG. 22 illustrates the trigger of FIG. 4 and the rack of FIG. 18 in a further partially retracted, or further partially returned, position.
Figure 28:
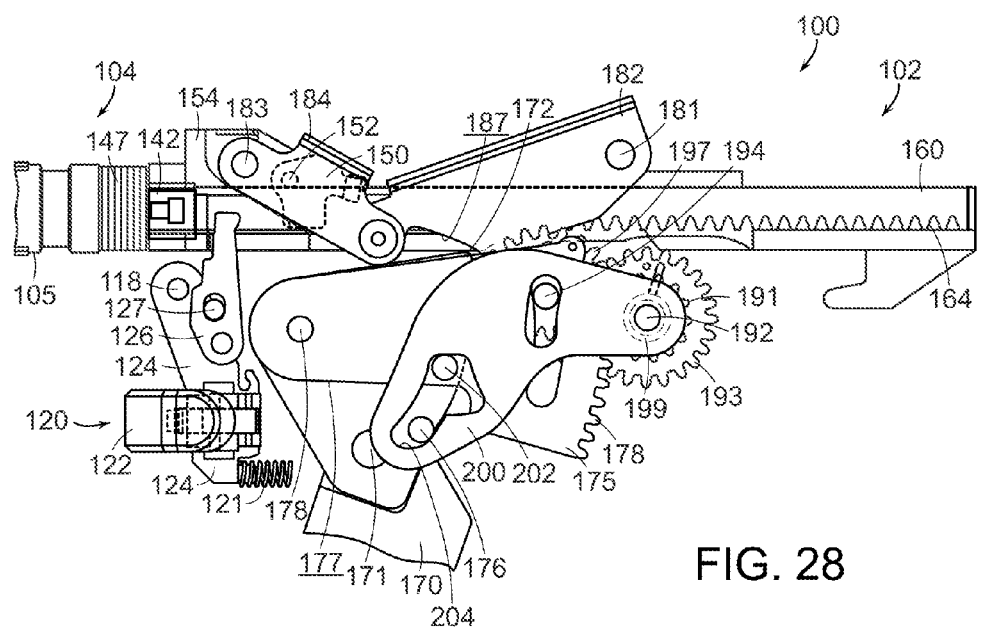
FIG. 28 illustrates the toggle clamp of FIG. 6 in an unactuated configuration and the rack of FIG. 18 in a fully retracted position.

Once the trigger 170 has been moved through its second range of motion and/or at any suitable moment during the second range of motion, the trigger 170 can be released. Upon the release of trigger 170, a return spring, such as torsion spring 199 (FIG. 28), for example, can reverse the rotation of compounding gears 191, 193, and 195 and pinion gear 197 in order to retract rack 160 and cutting member 140 in a proximal direction, i.e., in a direction opposite direction F. In at least one embodiment, referring to FIG. 28, one end of the torsion spring 199 can be engaged with the compounding gear 191 and another end of the torsion spring 199 can be engaged with the handle body 112, for example, such that potential energy stored within the torsion spring 199 when the rack 160 is advanced can be released when the trigger 170 is released in order to rotate compounding gear 191 in a reverse direction. In addition to the above, referring to FIG. 21 the reverse rotation of compounding gear 191 can, owing to the meshing engagement of trigger gear teeth 178 and compounding gear 191, rotate trigger gear 175 downwardly in a direction indicated by arrow G. In various embodiments, the downward rotation of trigger gear 175 can be transmitted to trigger 170 via the interaction of drive surface 177 acting against the drive pin 176 in order to retract, or return, the trigger 170 through its second range of motion, as illustrated in FIG. 22. In at least one embodiment, the surgical instrument can further comprise a reversing plate 200 which can be operably engaged with compounding gear 191 such that the reverse rotation of compounding gear 191 can also be transmitted to trigger gear 175 via reversing plate 200. The reversing plate 200 can be keyed to compounding gear 191 and/or pin 192 such that, as compounding gear 191 is driven in a reverse direction by return spring 199, the reversing plate 200 is driven downwardly and rotated about an axis defined by pin 192 in a direction indicated by arrow H. In such circumstances, referring to FIG. 22, the reversing plate 200 can act against drive pin 202 extending from trigger gear 175 to drive trigger gear 175 downwardly.

Figure 23:
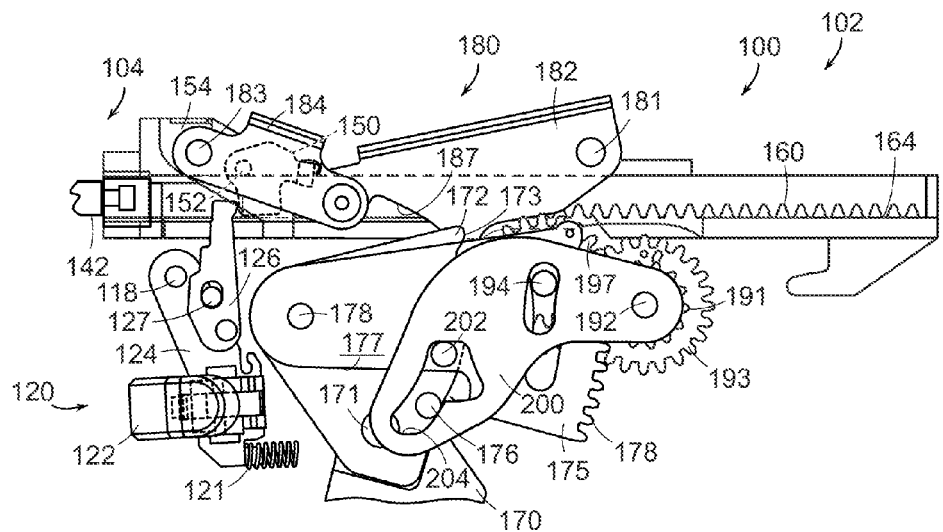
FIG. 23 illustrates the trigger of FIG. 4 engaged with the toggle clamp of FIG. 6 and the toggle clamp being moved from its fully actuated configuration to a partially actuated configuration.
Figure 24:
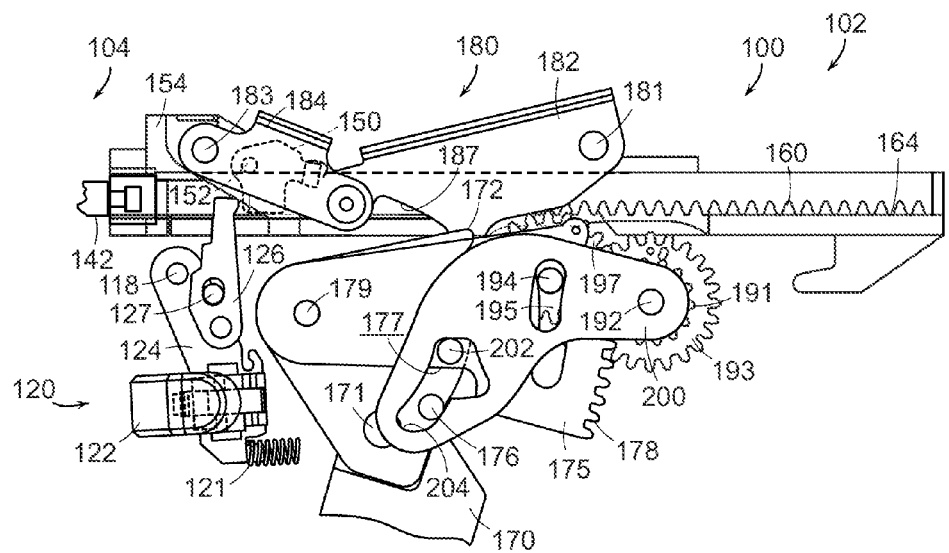
FIG. 24 illustrates the toggle clamp of FIG. 6 in a further partially actuated configuration and the rack of FIG. 18 in a further partially retracted, or further partially returned, position.
Figure 26:
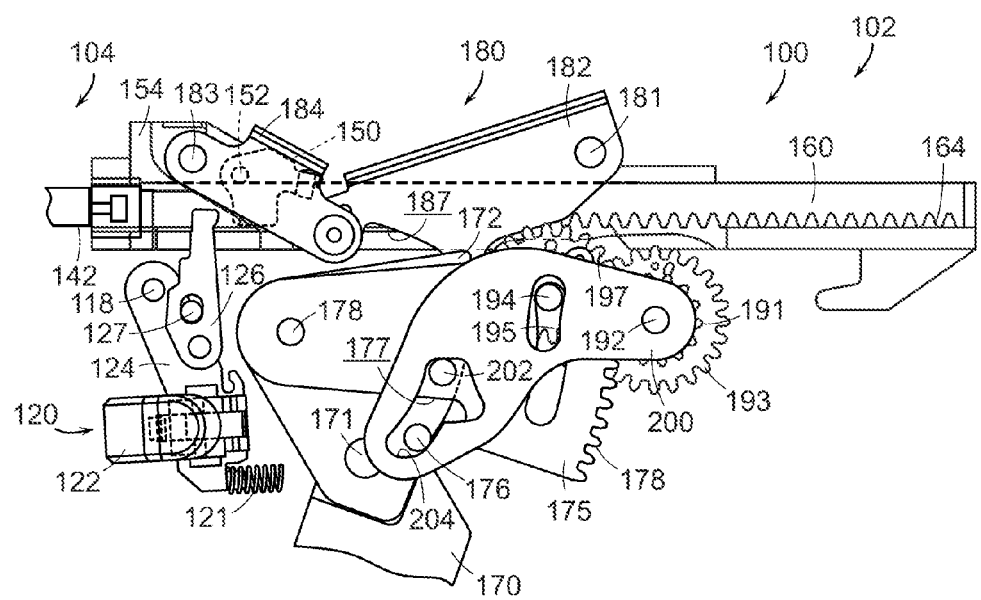
FIG. 26 illustrates the toggle clamp of FIG. 6 in an unactuated configuration.

In various embodiments, further to the above, the return spring 199, via gears 191, 193, 195, and 197, can return the cutting member 140 and the rack 160 from their third position to their second position and allow the rack lock 150 to re-engage the rack 160 as illustrated in FIG. 23. Owing to the re-engagement of rack lock 150 with rack 160, the yoke spring 147 can push yoke 154, rack 160, and cutting member 140 in a proximal direction, i.e., a direction opposite direction F. In various circumstances, the yoke spring 147, via yoke 154, can move the rack 160 and the cutting member 140 from their second positions to their first positions. In addition to the above, when yoke spring 147 pushes yoke 154 backward, the yoke 154 can drive, or collapse, the toggle clamp 180 between its second configuration (FIG. 22) into its first configuration (FIG. 23). In such circumstances, referring to FIGS. 23 and 24, the cam 172 extending from trigger 170 can become re-engaged with the pocket 173 in first link 182 such that the first link 182 can drive the trigger 170 through its first range of motion into its unactuated position as illustrated in FIG. 26.

Figure 25:
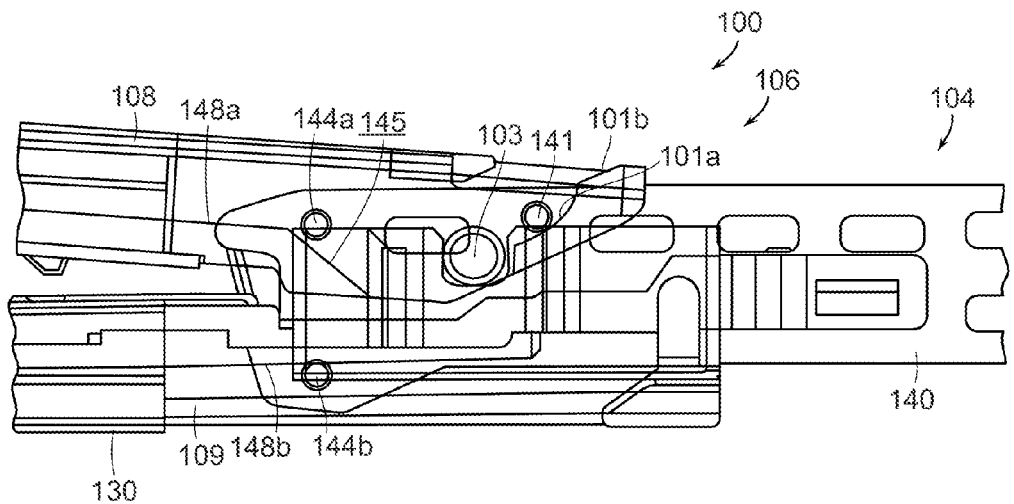
FIG. 25 illustrates the end effector of FIG. 3 in a partially opened position and the knife bar of FIG. 3 in a partially retracted position.
Figure 27:
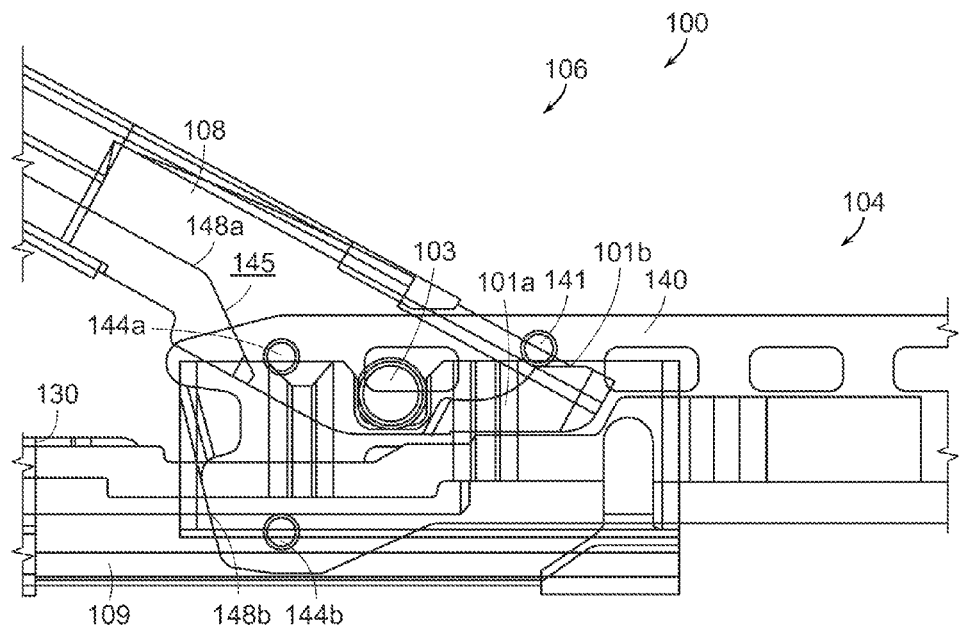
FIG. 27 illustrates the end effector of FIG. 3 in a fully opened position and the knife bar of FIG. 3 in a fully retracted position.

When the cutting member 140 is returned to its first position from its second position, as described above and referring to FIGS. 25 and 27, the cutting member 140 can move second jaw 109 from its closed position to its open position. More particularly, in at least one embodiment, the cutting member 140 can further comprise at least one opening cam pin 141 extending therefrom which, when moved proximally, can engage cam surface 101a on second jaw 109 such that second jaw 109 is pivoted upwardly about pivot pins 103 into its open position as illustrated in FIG. 27. Once jaw 109 has been moved into its open position, the cam pin 141 can be further retracted such that it is positioned over and/or against lock surface 101b which is positioned proximally with respect to cam surface 101a. In such circumstances, the second jaw 109 can be locked or held in an open position by cam pin 141. In any event, in order to assure that the cutting member 140 has been fully returned to its first position, the drive pin 176 extending from trigger 170 can engage the sidewall of a slot 204 in reversing plate 200 as trigger 170 is returned to its unactuated position. More particularly, the drive pin 176 can assure that the reversing plate 200, the compounding gears 191, 193, 195, and 197, and the rack 160 have been returned to their initial positions and, as a result, assure that cutting member 140 has been returned to its initial position.

As described above, the trigger 170 comprises a drive pin 176 which, at the end of the first range of motion of trigger 170, can contact the drive surface 177 of trigger gear 175 in order to move trigger gear 175 upwardly. In such circumstances, the trigger 170 and trigger gear 175 move together about a common axis of rotation defined by pivot 171. When trigger 170 is released and returned to its unactuated position, however, the trigger 170 and trigger gear 175 can, referring to FIGS. 21-24, for example, move independently of one another and rotate relative to one another. More particularly, the trigger 170 and trigger gear 175 can move relative to one another about a pivot 179 on trigger 170 as trigger 170 is returned to its unactuated position and as the surgical instrument 100 is reset to its initial configuration.

In various embodiments, referring now to FIG. 41, an alternative surgical instrument can comprise substantially the same components and systems as surgical instrument 100, although the alternative surgical instrument can comprise a trigger assembly 170' comprising a first portion 170a' and a second portion 170b'. In certain embodiments, relative movement between the first portion 170a' and the second portion 170b' is possible during the actuation of trigger 170'. More particularly, in at least one embodiment, a force overload mechanism can be positioned intermediate the first trigger portion 170a' and the second trigger portion 170b' such that, when the force applied to trigger portion 170a' exceeds a predetermined value, the trigger portion 170a' can move relative to the trigger portion 170b' and prevent any force in excess of the predetermined value from being transmitted to trigger gear 175 via drive pin 176'. Referring now to FIG. 42, the first trigger portion 170a' can comprise a pivot hole 171a' which can be aligned with, referring to FIG. 43, a pivot hole 171b' in second trigger portion 170b' wherein, when the first portion 170a' and the second portion 170b' are assembled together, as illustrated in FIG. 41, the first portion 170a' and the second portion 170b' can rotate together about an axis defined by pivot 171'. More particularly, a force, or load, FA applied to first portion 170a' can cause first portion 170a' to rotate about pivot 171' and, owing to drive pin 176', the rotation of first portion 170a' can be transmitted to second portion 170b' in order to cause second portion 170b' to be rotated about pivot 171'. In at least one embodiment, the drive pin 176' can be slidably positioned within a slot 212' within first portion 170a', wherein the first portion 170a' can further comprise a spring, such as an axial compression 216', for example, configured to bias the drive pin 176' against the end 214' of slot 212'. As illustrated in FIG. 41, the drive pin 176' can extend through a drive aperture 218' in second portion 170b', wherein, in various circumstances, at least a portion of the force FA applied to first trigger portion 170a' can be transmitted through the spring 216', drive pin 176', and a sidewall of drive aperture 218' in order to apply a force to second trigger portion 170b'.

In various embodiments, further to the above, the force transmitted between the first trigger portion 170a' and the second trigger portion 170b' can be represented by a force FT (FIG. 41) which is transmitted through spring 216. As illustrated in FIG. 41, the force FT can be aligned, or collinear, with the longitudinal, or axial, axis of spring 216'. When the force FT is at or below the predetermined, or threshold, value described above, the first portion 170a' and the second portion 170b' can move together with little, if any, relative movement therebetween. In at least one such embodiment, the spring 216' can be compressed between the drive pin 176' and a second sidewall 215' of the slot 212 such that the spring 216' is compressed by a preload force which is equal to, or at least substantially equal to, the predetermined threshold value. In such circumstances, the spring 216' may not be further compressed unless and if the force FT exceeds the predetermined threshold value. Once the force FT exceeds the predetermined threshold value, the spring 216' may be further compressed, thereby permitting relative movement between first portion 170a' and second portion 170b'. Furthermore, owing to such relative movement, the force in excess of the predetermined threshold value may be absorbed by the spring 216' instead of being transmitted to trigger gear 175 via drive pin 176'. Such embodiments can prevent an excessive force from being applied to rack 160 and cutting member 140 and, as a result, an overload condition can be avoided, or at least partially ameliorated.

Figure 44:
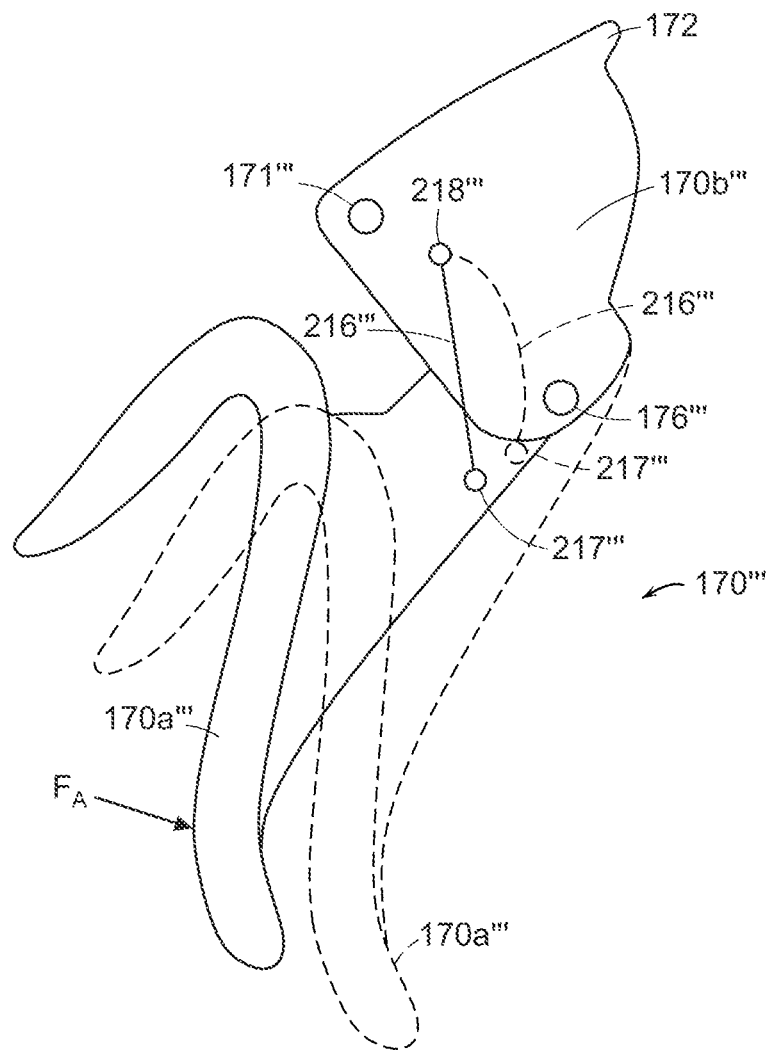
FIG. 44 illustrates a trigger assembly of an alternative embodiment of a surgical instrument, wherein the trigger assembly further comprises a mechanism for limiting the force that can be transmitted through the trigger assembly.

In various embodiments, referring now to FIG. 44, an alternative surgical instrument can comprise substantially the same components and systems as surgical instrument 100, although the alternative surgical instrument can comprise a trigger assembly 170''' comprising a first portion 170a''' and a second portion 170b'''. In certain embodiments, relative movement between the first portion 170a''' and the second portion 170b''' is possible during the actuation of trigger 170'''. Similar to the above, in at least one embodiment, a force overload mechanism can be positioned intermediate the first trigger portion 170a''' and the second trigger portion 170b''' such that, when the force applied to trigger portion 170a''' exceeds a predetermined value, the trigger portion 170a''' can move relative to the trigger portion 170b''' and prevent any force in excess of the predetermined value from being transmitted to trigger gear 175 via drive pin 176'''. Similar to the above, the first trigger portion 170a''' and the second trigger portion 170b''' can be pivotable about pivot pin 171''', wherein a force, or load, FA applied to first portion 170a''' can cause first portion 170a'' to rotate about pivot 171''' and, owing to beam, or link, 216''', the rotation of first portion 170a''' can be transmitted to second portion 170b''' in order to cause second portion 170b''' to be rotated about pivot 171'''. More particularly, in at least one embodiment, a first end 217''' of beam 216''' can be fixedly mounted to first trigger portion 170a''' and a second end 218''' of bean 216''' can be fixedly mounted to second trigger portion 170b''', wherein, in various circumstances, at least a portion of the force FA applied to first trigger portion 170a''' can be transmitted through the beam 216''' in order to apply a force to second trigger portion 170b'''.

In various embodiments, when the force transmitted through beam 216'' is at or below a predetermined, or threshold, value, the first portion 170a'' and the second portion 170b'' can move together with little, if any, relative movement therebetween. More particularly, the beam 216'' can be configured such that, although the below-threshold force transmitted through beam 216'' may create a compressive contraction or other minor elastic deformation within the beam 216'', the beam 216'' will remain largely undeflected as long as the force transmitted therethrough is below the threshold value. Once the force transmitted through beam 216'' exceeds the predetermined threshold value, however, the beam 216' may buckle, thereby permitting relative movement between first portion 170a' and second portion 170b'. Such relative movement is depicted in FIG. 44 which illustrates the first portion 170a'' in phantom lines as having moved relative to second trigger portion 170b''. In such circumstances, the first end 217'' can move toward the second end 218'' such that beam 216 buckles or collapses laterally. In various circumstances, such buckling can be elastic or resilient which could allow the first trigger portion 170a'' to be reset relative to the second trigger portion 170b''. In other circumstances, the buckling can be at least partially inelastic, or plastic, which may prevent or inhibit such a reset. In any event, the various embodiments described above can prevent an excessive force from being applied to rack 160 and cutting member 140 and, as a result, an overload condition can be avoided, or at least partially ameliorated.

Figure 29:
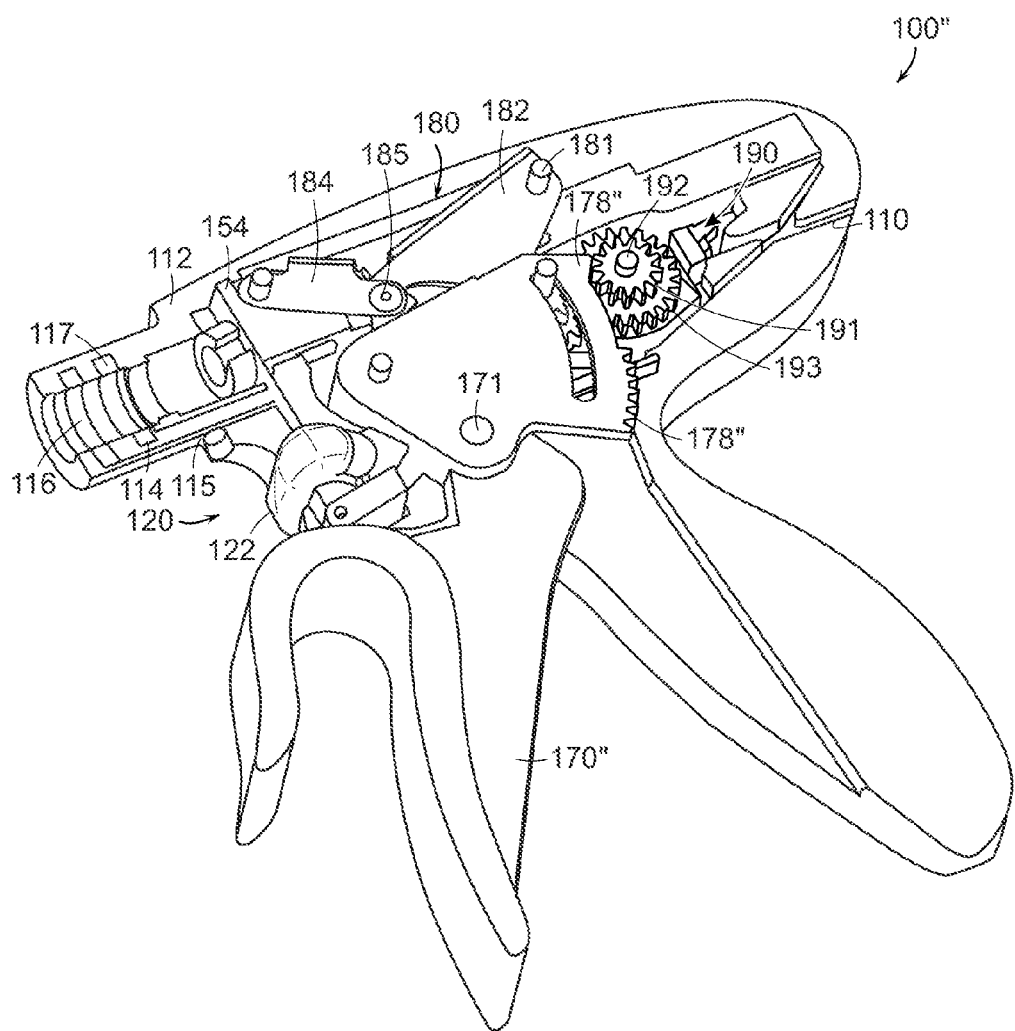
FIG. 29 is a perspective view of a handle of an alternative embodiment of a surgical instrument in an unactuated configuration illustrated with various components removed.
Figure 30:
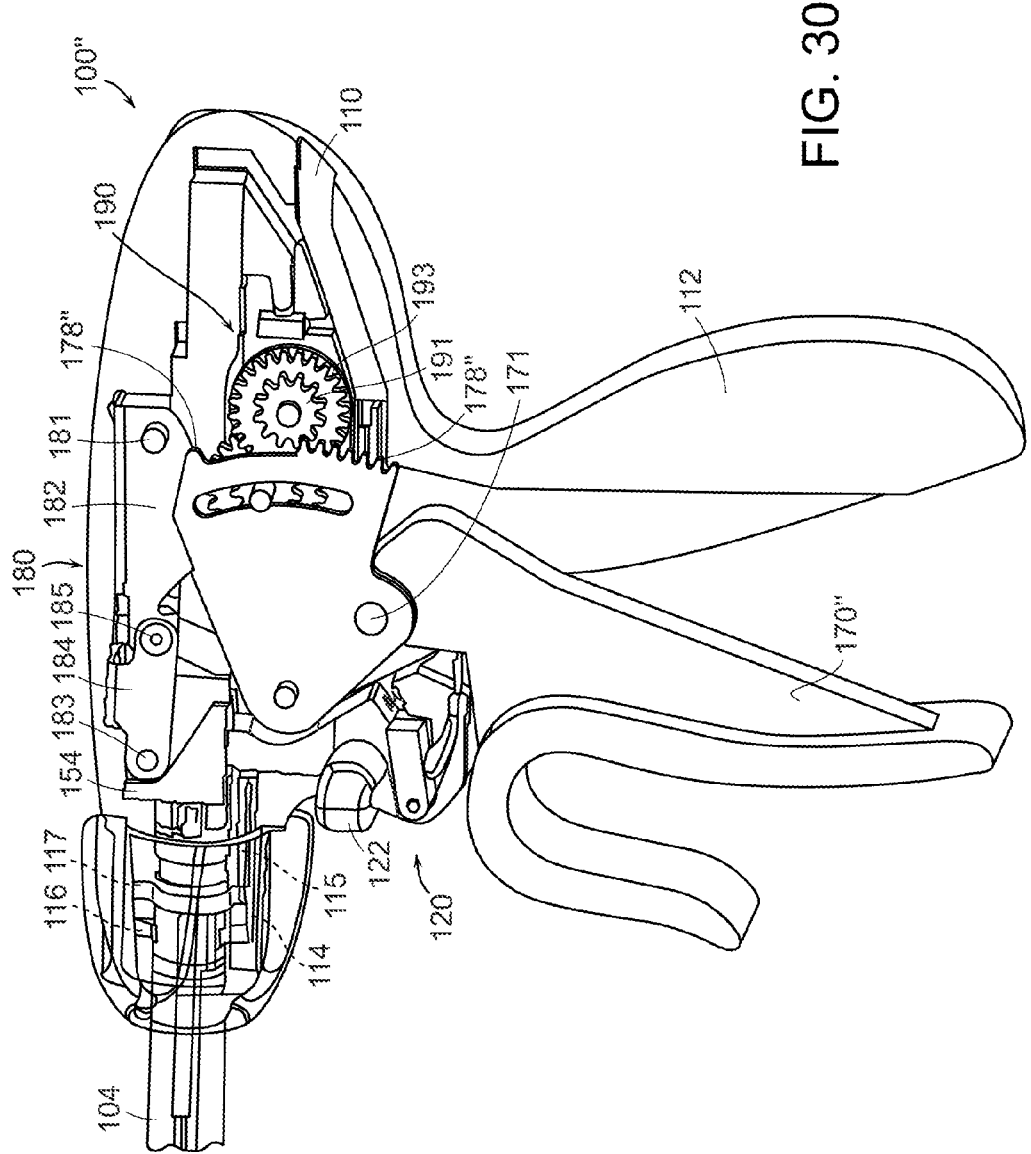
FIG. 30 is another perspective view of the handle of FIG. 29 in a partially actuated position illustrating a trigger coming into operative engagement with a gear of a second drive system.
Figure 31:
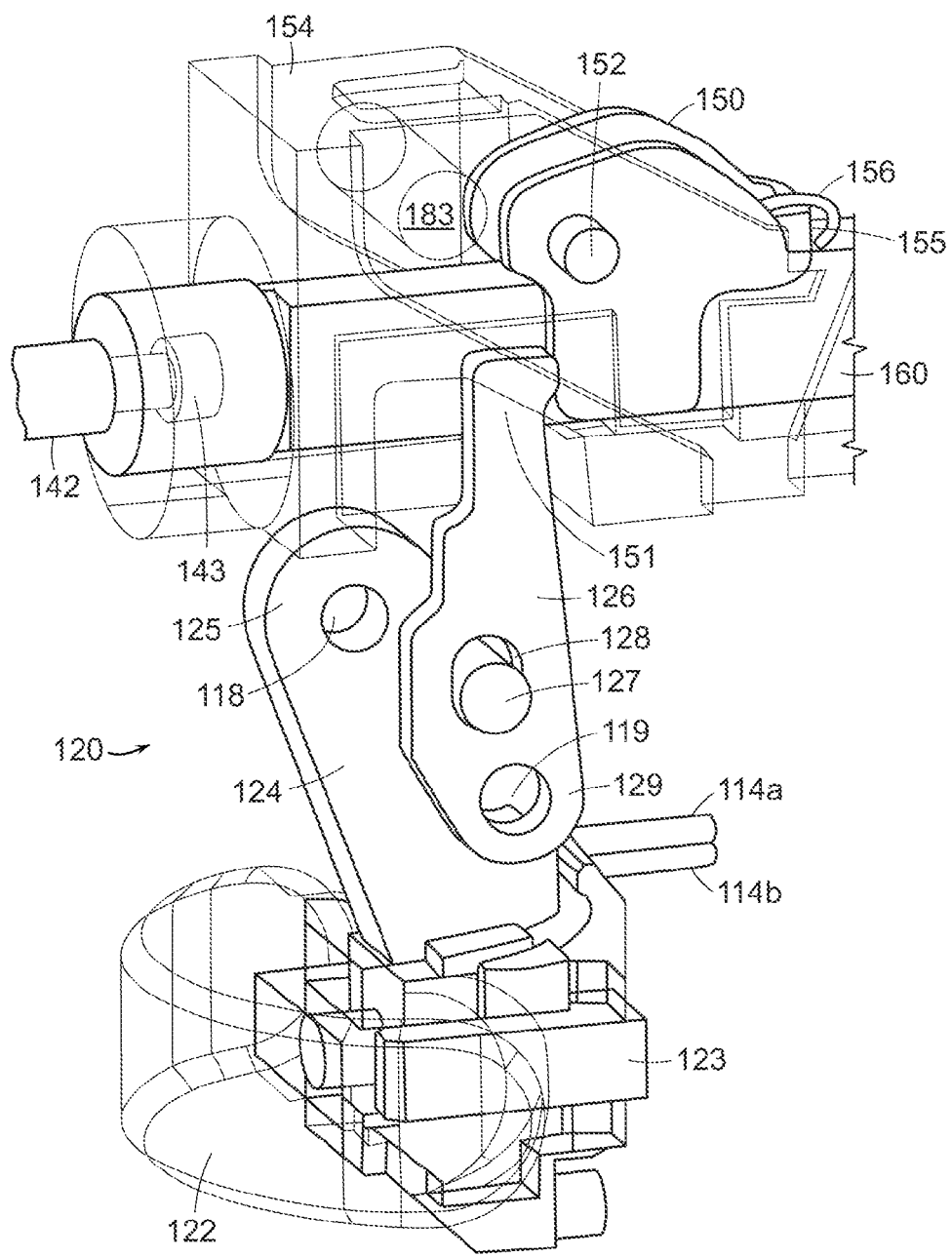
FIG. 31 is a perspective view of the lock system of FIG. 9 in an unactuated, but locked configuration with an alternative embodiment of a rack of the second drive system.

In various alternative embodiments, referring now to FIGS. 29 and 30, an alternative surgical instrument 100'' can comprise a one piece trigger 170'' which can drive the first drive system and the second drive system described above. More particularly, in at least one embodiment, the trigger 170'' can be, similar to the above, configured to be rotated between an actuated position and an unactuated position about pivot 171 during a stroke of trigger 170''. Also similar to the above, this stroke of trigger 170'' can comprise a first range of motion for driving the first drive system and a second range of motion for driving the second drive system. Referring to FIG. 29, the trigger 170'' is illustrated in an unactuated position wherein trigger gear teeth 178'' are not operably engaged with compounding gear 191 and the toggle clamp 180 is in its first, or unactuated, configuration. During the first range of motion of trigger 170'', referring now to FIG. 30, the trigger 170'' can move the toggle clamp 180 from its first configuration into its second configuration, similar to the above, and, in addition, operably engage trigger gear teeth 178'' with compounding gear 191. During the second range of motion of trigger 170'', similar to the above, the trigger 170'' can rotate compounding gear 191 to advance rack 160 and cutting member 140 and, as trigger 170'' is no longer operably engaged with toggle clamp 180, the trigger 170'' can move relative to first link 182. When trigger 170'' is released, similar to the above, the surgical instrument 100'' can comprise a spring which can bias toggle clamp 180 back into its first configuration and return trigger 170'' to its unactuated position. The surgical instrument 100'' can further comprise a second spring which can reverse the rotation of compounding gear 191 to return the rack 160 and cutting member 140 to their initial, or starting, positions. In various embodiments, the trigger 170'' can further comprise a return tooth 178'' which can be configured to engage compounding gear 191 and assure that compounding gear 191, rack 160, and cutting member 140 are returned to their initial, or starting, positions as trigger 170'' is moved into its unactuated position as illustrated in FIG. 29.

Figure 45:
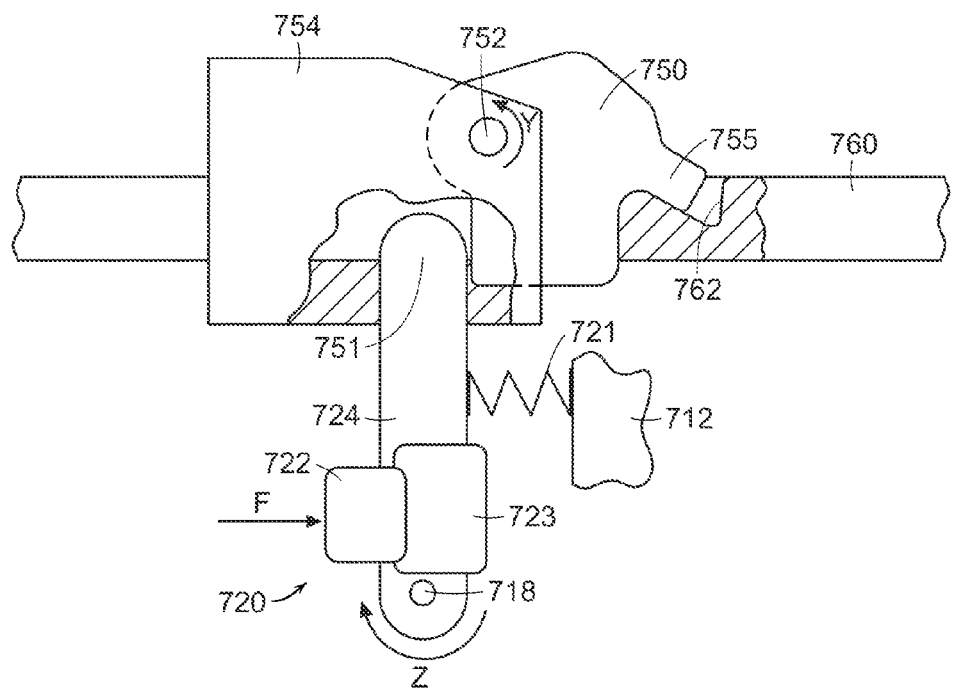
FIG. 45 is a diagram of an energy trigger assembly in accordance with at least one alternative embodiment of the present invention.

As described above, in various embodiments, the trigger assembly 120 can comprise a button 122 for actuating switch 123, wherein switch 123 is mounted to first link 124, wherein first link 124 is operably engaged with second link 126, and wherein second link 126 is configured to rotate lock 150. Referring now to the embodiment illustrated in FIG. 45, a surgical instrument can comprise a trigger assembly 720 comprising, similar to the above, a switch 723 mounted to a link 724, wherein the switch 723 can comprise a button 722 configured to actuate switch 723. In various embodiments, button 722 and switch 723 can operate in substantially the same manner as button 122 and switch 123; however, in at least one embodiment, the link 724 of trigger assembly 720 may be configured such that it can engage lock 750 directly, i.e., without the presence of a second link, such as second link 126, for example, operably positioned therebetween. In at least one such embodiment, a force F can be applied to button 722 in order to actuate the switch 723 and, simultaneously, rotate link 724 about pivot 718 in a direction indicated by arrow Z. In such circumstances, a drive end 751 of the link 724 can contact lock 750 and rotate lock 750 about pivot pin 752 of yoke 754 in a direction indicated by arrow Y. In various embodiments, further to the above, the force sufficient to actuate switch 723 may be sufficient to move lock 750 from its locked position (FIG. 45), in which lock tooth 755 is positioned within recess 762 in rack 760, into an unlocked position in which rack 760 can move relative to lock 750 and yoke 754. In at least one such embodiment, similar to the above, the stiffness of a spring within switch 723 and the stiffness of spring 721, positioned intermediate link 724 and handle frame 712, can be selected such that switch 723 is actuated at the same time, or at least substantially the same time, as rack 760 is unlocked. In various other embodiments, also similar to the above, the stiffness of spring 721 and the spring of switch 723 can be selected such that switch 723 can be actuated without moving lock 750 into an unlocked configuration. In such embodiments, a second, or larger, force could be applied to button 722 in order to unlock lock 750. In various alternative embodiments, the lock can include a lock spring configured to bias the lock 750 into a locked configuration and, in at least one embodiment, the lock spring can be used in lieu of spring 721, for example.

Figure 46:
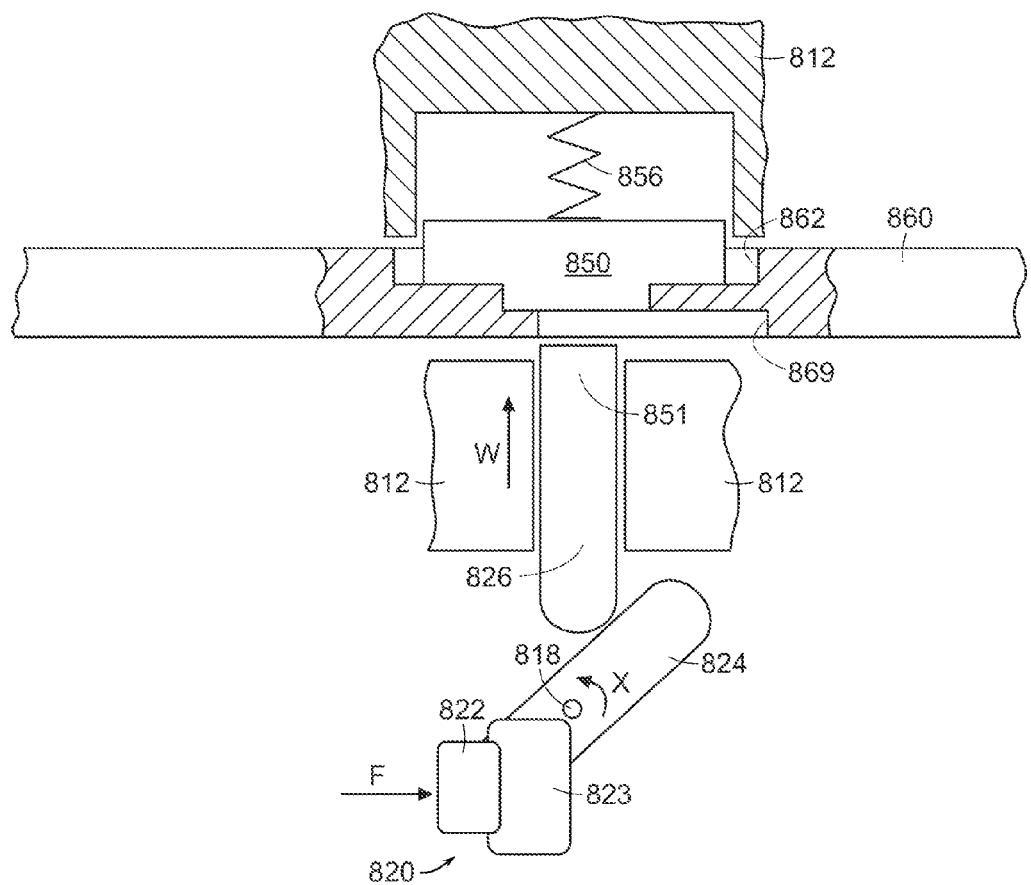
FIG. 46 is a diagram of another energy trigger assembly in accordance with at least one alternative embodiment of the present invention.

Referring now to the embodiment of FIG. 46, a surgical instrument can comprise a trigger assembly 820 comprising, similar to the above, a switch 823 comprising a button 822, wherein the switch 823 is mounted to a first link 824, and wherein upon an application of a force F to button 820, the force can rotate link 824 about pivot 818 in a direction indicated by arrow X. As illustrated in FIG. 46, the trigger assembly 820 can further comprise a slider 826 which is operably engaged with first link 824 such that, as link 824 is rotated in direction X, link 824 can drive slider 826 upwardly in a direction indicated by arrow W within a slot defined by handle portion 812. When slider 826 is moved upwardly, a drive end 851 of slider 826 can pass through a slot 869 in rack 860 in order to engage lock 850 and lift it upwardly out of recess 862 in rack 860. In various embodiments, further to the above, the trigger assembly 820 can further comprise a lock spring 856 positioned intermediate the lock 850, for example, and the handle frame 812 wherein the lock spring 856 can be configured to bias lock 850 into recess 862. In certain embodiments, similar to the above, the switch 823 can comprise a spring wherein the stiffness of the switch spring and the lock spring 856 can be selected such that the force sufficient to actuate switch 823 can be sufficient to move lock 850 into an unlocked position and, as a result, unlock rack 860. In various alternative embodiments, also similar to the above, the spring of switch 823 and lock spring 856 can be selected such that switch 823 can be actuated without moving lock 850 into an unlocked position. In such embodiments, a second, or larger, force could be applied to button 822 in order to unlock lock 850.

Figure 39:
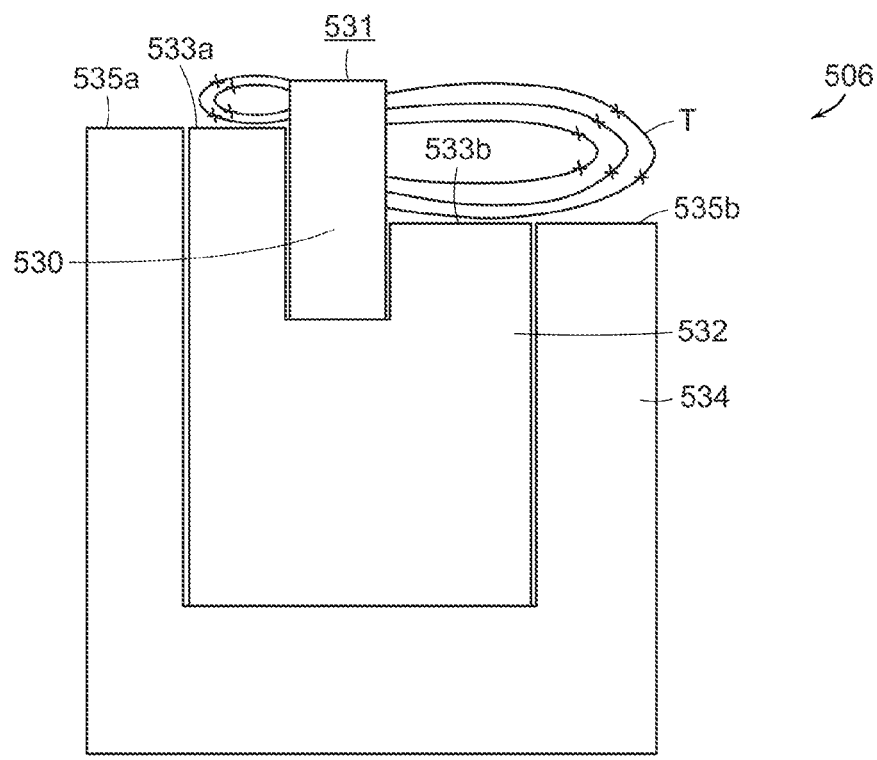
FIG. 39 illustrates a jaw of an end effector comprising a movable electrode.

In various embodiments, as described above, the end effector 106 of surgical instrument 100 can comprise an electrode 130 which, in co-operation with a ground or return electrode, can allow current to flow through tissue positioned within the end effector 106. In various circumstances, as also described above, the current flowing through the electrode 130 can generate heat within the electrode 130 in order to seal the tissue, for example. In at least one embodiment, the electrode 130 can be securely positioned within the first jaw 108, for example, such that the electrode 130 does not move relative to the first jaw 108. In addition to the above, the jaw 108 can comprise one or more insulators positioned intermediate the electrode 130 and the return electrode, wherein the insulators can assure that current does not flow directly between the electrode 130 and the return electrode without at least first passing through the tissue. In various alternative embodiments, referring now to FIG. 39, an alternative surgical instrument can comprise an electrode 530 which can be moved relative to an insulator 532 and/or a return 534, for example. In at least one embodiment, the electrode 530 can comprise a top surface, or tissue-contacting surface, 531 which can be configured to be positioned against the tissue T positioned within the end effector 506. In various circumstances, the top surface 531 of electrode 530 can be raised and/or lowered with respect to the insulator 532 and/or return 534. More particularly, in at least one such embodiment, the top surface 531 of electrode 530 can be moved relative to the top surfaces 533*a* and 533*b* of insulator 532 and/or relative to the top surfaces 535*a* and 535*b* of return 534. In various circumstances, raising the electrode 530, or top surface 531, relative to the insulator 532 and/or return 534 can increase the amount of tissue exposed to the electrode 530. In such circumstances, the size of the seal created within the tissue can be increased as compared to when the electrode 530 is in a lower position, for example. When the electrode 530 is lowered, the size of the seal created within the tissue can be decreased as compared to when the electrode 530 is in a raised position, for example. In various circumstances, when the electrode 530 is in a lower position, the lateral spread of heat to tissue adjacent the end effector 506 can be reduced as compared to when the electrode 530 is in a raised position.

In various embodiments, further to the above, a surgical instrument can comprise means for lifting and/or lowering electrode 530 relative to insulator 532. In at least one embodiment, the electrode 530 can comprise a bottom surface comprising a ramp or inclined surface, wherein, when the electrode 530 is slid longitudinally within the end effector 506, the inclined surface can contact a cam within the end effector 506 such that the electrode 530 is lifted upwardly, i.e., in a direction which is orthogonal, or at least substantially orthogonal, to a plane defined by one of top surfaces 531, 533*a*, 533*b*, 535*a*, and/or 535*b*, for example. In other circumstances, the electrode 530 can be lowered downwardly relative to the plane when the electrode 530 is slid or pulled down the cam. In various embodiments, the end effector 506 can comprise two or more electrodes which can be raised and/or lowered together or independently. In embodiments where the electrodes are raised or lowered together, the surgical instrument can comprise an actuator which moves the electrodes longitudinally within the end effector at the same time. In embodiments where the electrodes can be raised and/or lowered independently, the surgical instrument can comprise two or more actuators which can be actuated independently in order to independently move the electrodes. In various other embodiments, a surgical instrument can comprise one or more drivers comprising an inclined surface which are slid under the electrodes in a longitudinal direction and, depending on the direction the drivers are slid, the drivers can raise or lower the electrodes.

Figure 40:
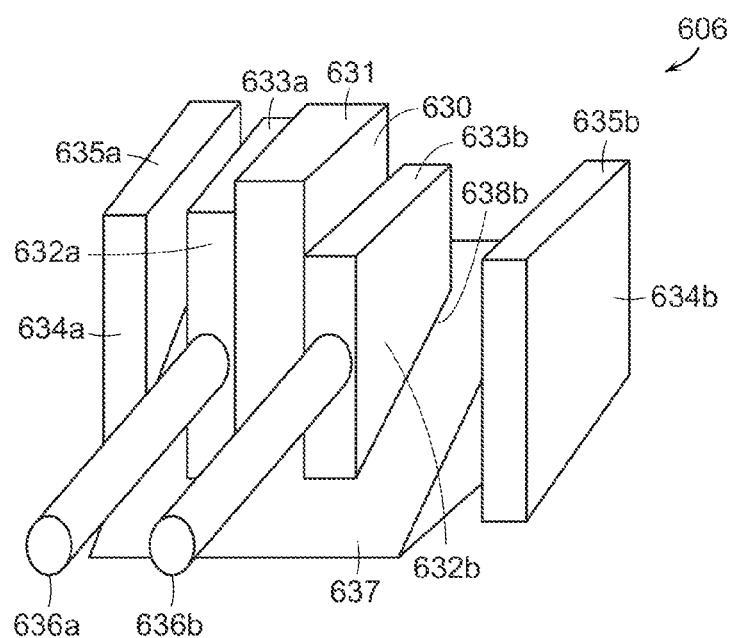
FIG. 40 illustrates a jaw of an end effector comprising first and second insulators which are movable relative to an electrode.

In various alternative embodiments, referring now to FIG. 40, an end effector 606 can comprise an electrode 630, a first insulator 632*a* positioned on a first side of electrode 630, a second insulator 632*b* positioned on a second side of electrode 630, a first return 634*a* positioned adjacent to first insulator 632*a*, and a second return 634*b* positioned adjacent to second insulator 632*b*. The end effector 606 can further comprise a first actuator 636*a* operably coupled to first insulator 632*a*, wherein the first actuator 636*a* can be configured to slide first insulator 632*a* up and/or down ramp, or cam, 637. Similarly, the end effector 606 can further comprise a second actuator 636*b* operably coupled to second insulator 632*b*, wherein the second actuator 636*b* can be configured to slide second insulator 632*b* up and/or down ramp, or cam, 637. As illustrated in FIG. 40, the second insulator 632*b* can comprise an inclined bottom surface 638*b* which can co-operate with the inclined surface of cam 673 in order to move top surface 633*b* of second insulator 632*b* relative to the top surface 631 of electrode 630 and/or the top surface 635*b* of return 634*b*, for example. Similarly, the first insulator 632*a* can comprise an inclined bottom surface which can co-operate with the inclined surface of cam 673 in order to move top surface 633*a* of first insulator 632*a* relative to the top surface 631 of electrode 630 and/or the top surface 635*a* of return 634*a*, for example. Various other embodiments are envisioned in which one or more returns can be raised and/or lowered relative to an electrode, for example.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument for supplying energy to tissue, comprising:
   a handle, comprising:
      a trigger; and
      an electrical input;
   a shaft extending from said handle, wherein said shaft comprises a conductor, wherein said trigger is selectively actuatable to electrically couple said electrical input and said conductor; and
   an end effector, comprising:
      a first jaw member;
      a second jaw member, wherein at least one of said first jaw member and said second jaw member is movable relative to the other of said first jaw member and said second jaw member to clamp tissue intermediate said first jaw member and said second jaw member;
      an electrode electrically coupled with said conductor, wherein said electrode is arranged relative to said first jaw member, wherein said electrode comprises:
         a contiguous electrode body configured to be polarized to a common polarity, wherein said contiguous electrode body comprises a polarizable contiguous tissue-facing surface; and
         a plurality of steam apertures defined within said polarizable contiguous tissue-facing surface, and wherein said electrode is configured to generate heat when electrical energy is supplied to said electrode; and
      at least one steam path within said contiguous electrode body, wherein said plurality of steam apertures are in fluid communication with said at least one steam path, and wherein said at least one steam path is configured to vent steam generated when the tissue is heated by said electrode.

2. The surgical instrument of claim 1, wherein said end effector further comprises a return electrode, wherein said shaft further comprises a return conductor, and wherein said return electrode comprises at least one steam path configured to vent steam generated when the tissue is heated.

3. The surgical instrument of claim 2, wherein said electrode and said return electrode are positioned within said first jaw member, wherein said first jaw member further comprises an insulator positioned intermediate said electrode and said return electrode, and wherein said insulator comprises at least one steam path configured to vent steam generated when the tissue is heated.

4. The surgical instrument of claim 1, wherein said end effector further comprises a moveable cutting member configured to transect the tissue positioned intermediate said first jaw member and said second jaw member, and wherein said cutting member comprises at least one steam path configured to vent steam generated when the tissue is heated.

5. A surgical instrument for supplying energy to tissue, comprising:
   a handle, comprising:
      a trigger; and
      an electrical input;
   a shaft extending from said handle, wherein said shaft comprises a conductor and a return conductor, wherein said trigger is selectively actuatable to electrically couple said electrical input and said conductor; and
   an end effector, comprising:
      a first jaw member;
      a second jaw member, wherein at least one of said first jaw member and said second jaw member is movable relative to the other of said first jaw member and said second jaw member to clamp tissue intermediate said first jaw member and said second jaw member;
      an electrode electrically coupled with said conductor, wherein said electrode is arranged relative to said first jaw member, and wherein said electrode is configured to generate heat when electrical energy is supplied to said electrode;
      a return electrode electrically coupled with said return conductor, wherein said return electrode comprises:
         a contiguous electrode body comprising a polarizable contiguous tissue-facing surface; and
         a plurality of steam apertures defined within said polarizable contiguous tissue-facing surface; and
      at least one steam path within said return electrode, wherein said plurality of steam apertures are in fluid communication with said at least one steam path, and wherein said at least one steam path is configured to vent steam generated when the tissue is heated by said electrode.

6. The surgical instrument of claim 5, wherein said electrode and said return electrode are positioned within said first jaw member, wherein said first jaw member further comprises an insulator positioned intermediate said electrode and said return electrode, and wherein said insulator comprises at least one steam path configured to vent steam generated when the tissue is heated.

7. The surgical instrument of claim 5, wherein said end effector further comprises a moveable cutting member configured to transect the tissue positioned intermediate said first jaw member and said second jaw member, and wherein said cutting member comprises at least one steam path configured to vent steam generated when the tissue is heated.

8. A surgical instrument for supplying energy to tissue, comprising:
   a handle, comprising:
      a trigger; and
      an electrical input;
   a conductor, wherein said trigger is selectively actuatable to electrically couple said electrical input and said conductor; and
   an end effector, comprising:
      a first jaw member;
      a second jaw member, wherein at least one of said first jaw member and said second jaw member is movable relative to the other of said first jaw member and said second jaw member to clamp tissue intermediate said first jaw member and said second jaw member;
      an electrode electrically coupled with said conductor, wherein said electrode is arranged relative to said first jaw member, wherein said electrode is configured to generate heat when electrical energy is supplied to said electrode, and wherein said electrode comprises:
         a continuous electrode body configured to be polarized to a common polarity, wherein said continuous electrode body comprises a polarizable continuous tissue-facing surface; and
      steam conduction means for conducting steam generated when the tissue is heated by the electrode, wherein said steam conduction means is disposed entirely within said electrode and conducts the steam through said electrode.

9. The surgical instrument of claim 8, wherein said steam conduction means comprises at least one passage extending from said polarizable continuous tissue-facing surface through said continuous electrode body.

10. The surgical instrument of claim 8, wherein said steam conduction means comprises at least one channel in said continuous electrode body.

11. The surgical instrument of claim 8, wherein said surgical instrument further comprises a shaft, wherein said end effector further comprises a return electrode, wherein said shaft further comprises a return conductor, and wherein said return electrode comprises steam conduction means for venting steam generated when the tissue is heated.

12. The surgical instrument of claim 11, wherein said electrode and said return electrode are positioned within said first jaw member, wherein said first jaw member further comprises an insulator positioned intermediate said electrode and said return electrode, and wherein said insulator comprises steam conduction means for venting steam generated when the tissue is heated.

13. The surgical instrument of claim 8, wherein said end effector further comprises a moveable cutting member configured to transect the tissue positioned intermediate said first jaw member and said second jaw member, and wherein said cutting member comprises steam conduction means for venting steam generated when the tissue is heated.

* * * * *